(12) United States Patent
Guenther et al.

(10) Patent No.: US 12,091,386 B2
(45) Date of Patent: *Sep. 17, 2024

(54) D-AMPHETAMINE COMPOUNDS, COMPOSITIONS, AND PROCESSES FOR MAKING AND USING THE SAME

(71) Applicant: Zevra Therapeutics, Inc., Celebration, FL (US)

(72) Inventors: Sven Guenther, Coralville, IA (US); Guochen Chi, Coralville, IA (US); Travis Mickle, Kissimme, FL (US)

(73) Assignee: ZEVRA THERAPEUTICS, INC., Celebration, FL (US)

( * ) Notice: Subject to any disclaimer, the term of this patent is extended or adjusted under 35 U.S.C. 154(b) by 117 days.

This patent is subject to a terminal disclaimer.

(21) Appl. No.: 17/500,680

(22) Filed: Oct. 13, 2021

(65) Prior Publication Data

US 2022/0064116 A1    Mar. 3, 2022

Related U.S. Application Data

(63) Continuation of application No. 16/667,807, filed on Oct. 29, 2019, now Pat. No. 11,174,229.

(60) Provisional application No. 62/800,494, filed on Feb. 2, 2019, provisional application No. 62/752,324, filed on Oct. 29, 2018.

(51) Int. Cl.
| | |
|---|---|
| C07D 213/56 | (2006.01) |
| A61K 9/00 | (2006.01) |
| A61K 31/44 | (2006.01) |
| A61K 31/4458 | (2006.01) |
| A61K 31/4545 | (2006.01) |
| A61K 47/55 | (2017.01) |
| C07D 213/79 | (2006.01) |
| C07D 213/80 | (2006.01) |
| C07D 213/81 | (2006.01) |
| C07D 401/06 | (2006.01) |
| C07D 413/06 | (2006.01) |
| A61K 9/02 | (2006.01) |

(52) U.S. Cl.
CPC .......... *C07D 213/79* (2013.01); *A61K 9/0019* (2013.01); *A61K 9/0043* (2013.01); *A61K 31/4458* (2013.01); *A61K 31/4545* (2013.01); *A61K 47/55* (2017.08); *C07D 213/80* (2013.01); *C07D 213/81* (2013.01); *C07D 401/06* (2013.01); *C07D 413/06* (2013.01); *A61K 9/0053* (2013.01); *A61K 9/02* (2013.01)

(58) Field of Classification Search
CPC ... C07D 213/56; A61K 31/4425; A61K 31/44
USPC ................. 546/316; 514/355, 356
See application file for complete search history.

(56) References Cited

U.S. PATENT DOCUMENTS

| | | | |
|---|---|---|---|
| 11,174,229 B2* | 11/2021 | Guenther | A61K 31/4458 |
| 2009/0186828 A1 | 7/2009 | Mickle | |
| 2010/0303903 A1 | 12/2010 | Hackett | |
| 2015/0025027 A1 | 1/2015 | Moreira et al. | |
| 2019/0142815 A1 | 5/2019 | Guenther | |
| 2019/0284166 A1 | 9/2019 | Mickle et al. | |

FOREIGN PATENT DOCUMENTS

| | | |
|---|---|---|
| RU | 2573835 | 1/2016 |
| WO | 2002042276 A1 | 5/2002 |
| WO | 2007022535 | 2/2007 |
| WO | 2014002039 A1 | 1/2014 |
| WO | 2014054058 A2 | 4/2014 |
| WO | 2018191219 | 10/2018 |
| WO | 2020070557 A1 | 4/2020 |

OTHER PUBLICATIONS

International Search Report and Written Opinion regarding PCT Application No. PCT/US2020/019140, dated May 26, 2020, 13 pages.
Braeckman, R, et al., Single-dose Pharmacokinetics of KP415, an Investigational Product Containing the Prodrug Serdexmethylphenidate (SDX), in Children and Adolescents with ADHD; American Professional Society of ADHD and Related Disorders Poster, Washington, D.C., dated Jan. 20, 2019.

(Continued)

*Primary Examiner* — Charanjit Aulakh
(74) *Attorney, Agent, or Firm* — McAndrews, Held & Malloy, Ltd.

(57) ABSTRACT

Disclosed are d-amphetamine compounds and compositions comprising at least one organic acid covalently bound to d-amphetamine, having the structure of Formula IB

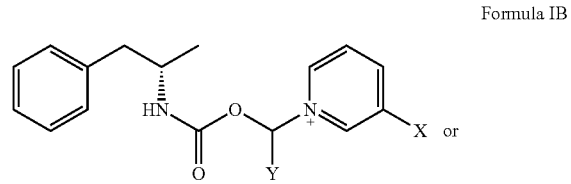

or Formula ID

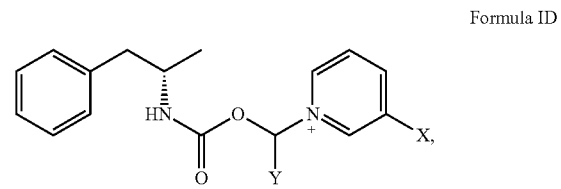

a salt thereof, a derivative thereof, or a combination thereof. Methods of making and using the same are also disclosed.

19 Claims, 10 Drawing Sheets

(56) References Cited

OTHER PUBLICATIONS

PCT, International Preliminary Report on Patentability regarding Application No. PCT/US2020/019140, dated May 12, 2022, 10 pages.
PCT, International Preliminary Report on Patentability regarding Application No. PCT/US2020/019146, dated May 12, 2022, 10 pages.
Russian Patent Office, Office Action regarding Application No. 2022114174, 16 pages, dated Jul. 24, 2023.
European Patent Office, "Extended European Search Report," regarding Application No. 20882891.3, 8 pages, Nov. 28, 2023.

* cited by examiner

D-AMPHETAMINE COMPOUNDS, COMPOSITIONS, AND PROCESSES FOR MAKING AND USING THE SAME

RELATED APPLICATIONS

The present patent application is a continuation of U.S. patent application Ser. No. 16/667,807, which was filed Oct. 29, 2019 and is related to and claims the priority benefit of U.S. Provisional Patent Application Ser. No. 62/800,494, filed Feb. 2, 2019 and U.S. Provisional Patent Application Ser. No. 62/752,324, filed Oct. 29, 2018 the content of which is hereby incorporated by reference in its entirety into this disclosure.

FEDERALLY SPONSORED RESEARCH OR DEVELOPMENT

[Not Applicable]

BACKGROUND

The presently described technology relates to novel compounds and compositions of d-amphetamine (i.e., 1-phenylpropan-2-amine), including organic compounds covalently bonded or attached to d-amphetamine, salts thereof, derivatives thereof, or combinations thereof. Methods of making and using the compounds and compositions of the present technology are also disclosed.

Stimulants, including d-amphetamine and its derivatives, enhance the activity of the sympathetic nervous system and/or central nervous system (CNS) and are prescribed for the treatment of a range of conditions and disorders predominantly encompassing, for example, attention deficit hyperactivity disorder (ADHD), attention deficit disorder (ADD), obesity, narcolepsy, appetite suppression, depression, anxiety, and wakefulness.

Attention deficit hyperactivity disorder (ADHD) in children has been treated with stimulants for many years. However, more recently, the increase in a number of prescriptions for ADHD therapy in the adult population has, at times, outperformed the growth of the pediatric market. Although there are various drugs currently in use for the treatment of ADHD, such as methylphenidate (commercially available from, for example, Novartis International AG (located in Basel, Switzerland) under the trademark Ritalin®) and non-stimulant atomoxetine (commercially from Eli Lilly and Company (located in Indianapolis, Ind.) as Strattera®), d-amphetamine has been the forerunner in ADHD therapy.

Initial drug therapy for ADHD was limited to fast-acting immediate release formulations of stimulants (e.g., Dexedrine®, pure dextroamphetamine sulfate, commercially available from Smith Kline and French located in the United Kingdom) which triggered an array of potentially undesirable side effects including, for example, fast wear-off of the therapeutic effect of the stimulant active ingredient causing rebound symptoms, cardiovascular stress/disorders (e.g., increased heart rate, hypertension, cardiomyopathy), other side effects (e.g., insomnia, euphoria, psychotic episodes), addiction and abuse.

Behavioral deterioration (rebound/"crashing") is observed in a significant portion of children with ADHD as the medication wears off, typically in the afternoon or early evening. Rebound symptoms include, for example, irritability, crankiness, hyperactivity worse than in the unmediated state, sadness, crying and in rare cases psychotic episodes. The symptoms may subside quickly or last several hours. Some patients may experience rebound/crashing so severe that treatment must be discontinued. Rebound/crashing effects can also give rise to addictive behavior by enticing patients to administer additional doses of stimulant with the intent to prevent anticipated rebound/crashing negative outcomes and side effects.

Stimulants, such as methylphenidate and d-amphetamine, have been shown to exhibit noradrenergic and dopaminergic effects that can lead to cardiovascular events comprising, for example, increased heart rate, hypertension, palpitations, tachycardia and in isolated cases cardiomyopathy, stroke, myocardial infarction, and sudden death. Consequently, currently available stimulants expose patients with pre-existing structural cardiac abnormalities or other severe cardiac indications to even greater health risks and are frequently not used or used with caution in this population. It is notable, however that the cardiovascular effects of stimulants, for example on heart rate and blood pressure, are dependent on the administered dose. As a result, a treatment which maintains the lowest effective stimulant blood concentrations for a therapeutically beneficial duration is believed to demonstrate fewer cardiovascular risks.

D-amphetamine and many of its derivatives (e.g., methamphetamine, 3,4-methylenedioxy-methamphetamine/"ecstasy") are widely abused for various purposes such as euphoria, extended periods of alertness/wakefulness, or rapid weight loss or by actual ADHD patients who developed excessive self-dosing habits to prevent rebound symptoms from manifesting, for example, in anxiety or depression. The effects desired by potential abusers originated from the stimulation of the central nervous system and prompted a Schedule II or even Schedule I classification for d-amphetamine (d- and 1-d-amphetamine individually and any combination of both are Schedule II) and certain derivatives thereof after the passage of the Controlled Substance Act (CSA) in 1970. Both classifications are defined by the high propensity for abuse. Schedule II drugs have an accepted medical use while Schedule I substances do not fall under the CSA. So far, all d-amphetamine products, including compositions with sustained release formulations thereof, are obligated to include a black box warning on the drug label to inform patients about the potential for d-amphetamine abuse and dependence.

It has been shown in the conventional art that most side effects of amphetamines are caused by a large initial spike in blood concentration of the stimulant which quickly erodes to levels below therapeutic effectiveness (typically within 4-6 hours). As a consequence, the high potency of dextroamphetamine (d-amphetamine) was subsequently modulated by a series of new drugs with increasingly sustained release profiles achieved by delivering d-amphetamine more slowly into the bloodstream with the goal to create safer and less abusable treatment outcomes and regimens. The methods and technologies for generating smaller spikes in drug blood concentrations include, for example, use of mixed salts and isomer compositions (i.e., different salts of d- and less potent 1-amphetamine), extended/controlled/sustained release formulations of amphetamine/dextroamphetamine salts (e.g., Adderall XR® commercially available from Shire U.S., Inc. located in Wayne, Pa.) and prodrugs of lisdexamfetamine salts (Vyvanse® also commercially available from Shire).

As a result, there still exists a need within the art for a safer dosage form of d-amphetamine and treatment regimen that is therapeutically effective and can provide sustained release and sustained therapeutic effect.

BRIEF SUMMARY

The presently described technology provides, in part, novel compounds, and compositions of the stimulant d-amphetamine ("d-Amp", "dextroamphetamine"), salts thereof, other derivatives thereof, and combinations thereof.

In some aspects, the present technology provides compounds and/or compositions comprising d-amphetamine and one or more organic compounds. In some aspects of the present technology, the organic compound comprises a heterocyclic nitrogen compound. Heterocyclic nitrogen compounds are commonly found in nature and are involved in several biological functions in plants and animals. Examples of heterocyclic nitrogen compounds for use in the practice of the present technology include, but are not limited to, for example, pyridine derivatives, some of which play an important role in the nicotinate and tryptophan metabolism. In these compounds, one carbon of the phenyl ring is commonly replaced by a nitrogen atom.

In some aspects of the present technology, the organic compound comprises an amino acid. Amino acids are organic compounds containing both a carboxyl (—COOH) and amino (—$NH_2$) group, and a variable side chain group. Amino acids that may be used in the present technology can be natural, standard, non-standard, unusual, synthetic, and/or essential amino acids, and can be an L-amino acid or a D-amino acid, or a combination thereof. Examples of amino acids for use in the practice of the present technology include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, homoarginine, citrulline, homocitrulline, homoserine, theanine, γ-aminobutyric acid, 6-aminohexanoic acid, sarcosine, carnitine, 2-aminoadipic acid, pantothenic acid, taurine, hypotaurine, lanthionine, thiocysteine, cystathionine, homocysteine, β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), 2-aminoisobutyric acid, isovaline, di-N-ethylglycine, N-methyl-alanine, L-abrine, 4-hydroxyproline, 5-hydroxylysine, 3-hydroxyleucine, 4-hydroxyisoleucine, 5-hydroxy-L-tryptophan, 1-aminocyclopropyl-1-carboxylic acid, azetidine-2-carboxylic acid, pipecolic acid, allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino-propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, 4-(dimethylamino)cinnamic acid, 2-pyridylalanine (2-Pal), and 3-pyridylalanine (3-Pal).

In some aspects, the compound has the structure of Formula IB:

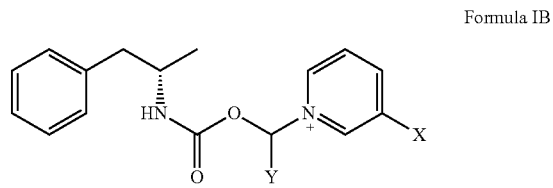

Formula IB where X is A-COO—R;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula ID

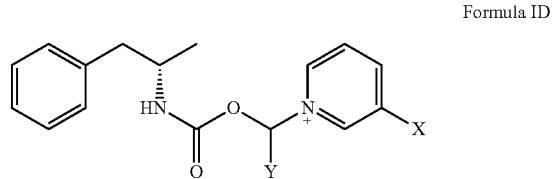

Formula ID where X is A-CO—NR¹R²;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and
where R¹ and R² are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

It should be appreciated that the carbon atom attached to Y is a chiral center if Y is not hydrogen.

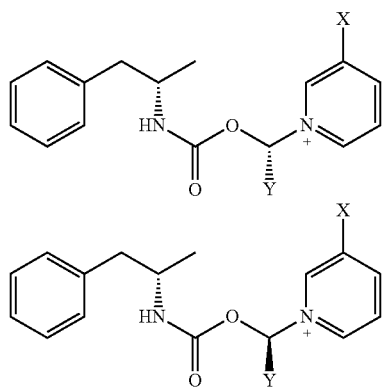

In some aspects, the present technology comprises conjugates where this chiral carbon has an R configuration. In other aspects, the present technology comprises conjugates where this chiral carbon has an S configuration. In further aspects, the present technology comprises a mixture of stereoisomers where some conjugates contain a chiral carbon having an R configuration and some conjugates contain a chiral carbon having an S configuration.

The presently described technology further provides methods of controlled therapeutic delivery of d-amphetamine compositions by oral administration. In at least one aspect, the presently described technology is focused on a slow/sustained controlled release composition of d-amphetamine, in compound form, that allows slow/sustained/controlled delivery of the stimulant into the blood system of a human or animal within a safe therapeutic window upon oral administration. At least some compositions/formulations of the current technology can lessen the rebound effect, cardiovascular stress, addiction/abuse potential and/or other common stimulant side effects associated with d-amphetamine and similar compounds. Such compositions may also increase the duration of therapeutic efficacy, ease of application, patient compliance and/or any combination of these characteristics when administered, in particular, orally.

The release of d-amphetamine following oral administration of the compounds of the present technology can occur gradually over an extended period of time thereby eliminating unintended excessive rapid elevations (e.g., large blood level concentration spikes) of drug levels in the bloodstream of a human or animal patient. Not wanting to be bound by any particular theory, it is also believed that such spikes in blood levels can lead to a euphoric drug "high" and cardiovascular effects like increased blood pressure and heart rate. Additionally, sustained blood levels are achieved within an effective therapeutic range for a longer duration than other conventional therapies, thereby preventing a rebound effect.

In some embodiments, the present technology provides particular d-amphetamine ("d-Amp", "dexamphetamine") compounds, compositions, or pharmaceutically acceptable salts thereof, to provide, for example, at least one single daily dose form of a d-amphetamine compound in a composition with unconjugated d-amphetamine that can provide both immediate and extended release PK profiles when compared to unconjugated d-amphetamine. The release profile in some instances provides the ability of the compound or composition to be administered using dosing regimens that are not easily utilized with the unconjugated d-amphetamine.

At least some compositions comprising the d-amphetamine compounds of the present technology are resistant to abuse by parenteral routes of administration, such as intravenous "shooting," intranasal "snorting," or inhalation "smoking," that are often employed during illicit use. The present technology thus provides a stimulant based treatment modality and dosage form for certain disorders requiring the stimulation of the CNS such as ADHD, ADD, obesity, narcolepsy, appetite suppressant, depression, anxiety, sleep disorders, excessive daytime sleepiness, insomnia, binge eating, and wakefulness with reduced or prevented abuse potential. Although not wanting to be bound by any particular theory, it is believed that compositions of the present technology result in substantially decreased abuse potential or abuse liability as compared to existing stimulant treatment modalities and dosage forms."

At least some compositions comprising the d-amphetamine compound of the present technology can also be used for treating stimulant (cocaine, methamphetamine) abuse and addiction, substance use disorder, improving battlefield alertness, and/or for combating fatigue.

The compositions of the present technology preferably have no or a substantially decreased pharmacological activity when administered through injection or intranasal routes of administration. However, they remain orally bioavailable with respect to d-amphetamine. The bioavailability can be a result of the hydrolysis of the covalent linkage between d-amphetamine and the remaining portion of the conjugate following oral administration. Hydrolysis is time-dependent, thereby allowing d-amphetamine and other metabolites such as p-hydroxyamphetamine and p-hydroxyephedrine to become available in its active form over an extended period of time. In at least one further aspect, release of d-amphetamine is diminished when compared to unconjugated d-amphetamine or eliminated when the composition of the present technology is delivered by parenteral routes.

For example, in one aspect, the composition of the present technology maintains its effectiveness and abuse resistance following the crushing of the tablet, capsule or other oral dosage form utilized to deliver the therapeutic component (i.e., active ingredient/drug) due to the controlled release components being a designed property of the composition, not the formulation. In contrast, conventional extended release formulations used to control the release of d-amphetamine are subject to release of up to the entire d-amphetamine content immediately following crushing. When the content of the crushed tablet is injected or snorted, the large dose of d-amphetamine produces the "rush" effect sought by addicts.

Other objects, advantages, and aspects of the invention are described below and will be obvious from this description and practice of the invention.

DETAILED DESCRIPTION

Figure 1:
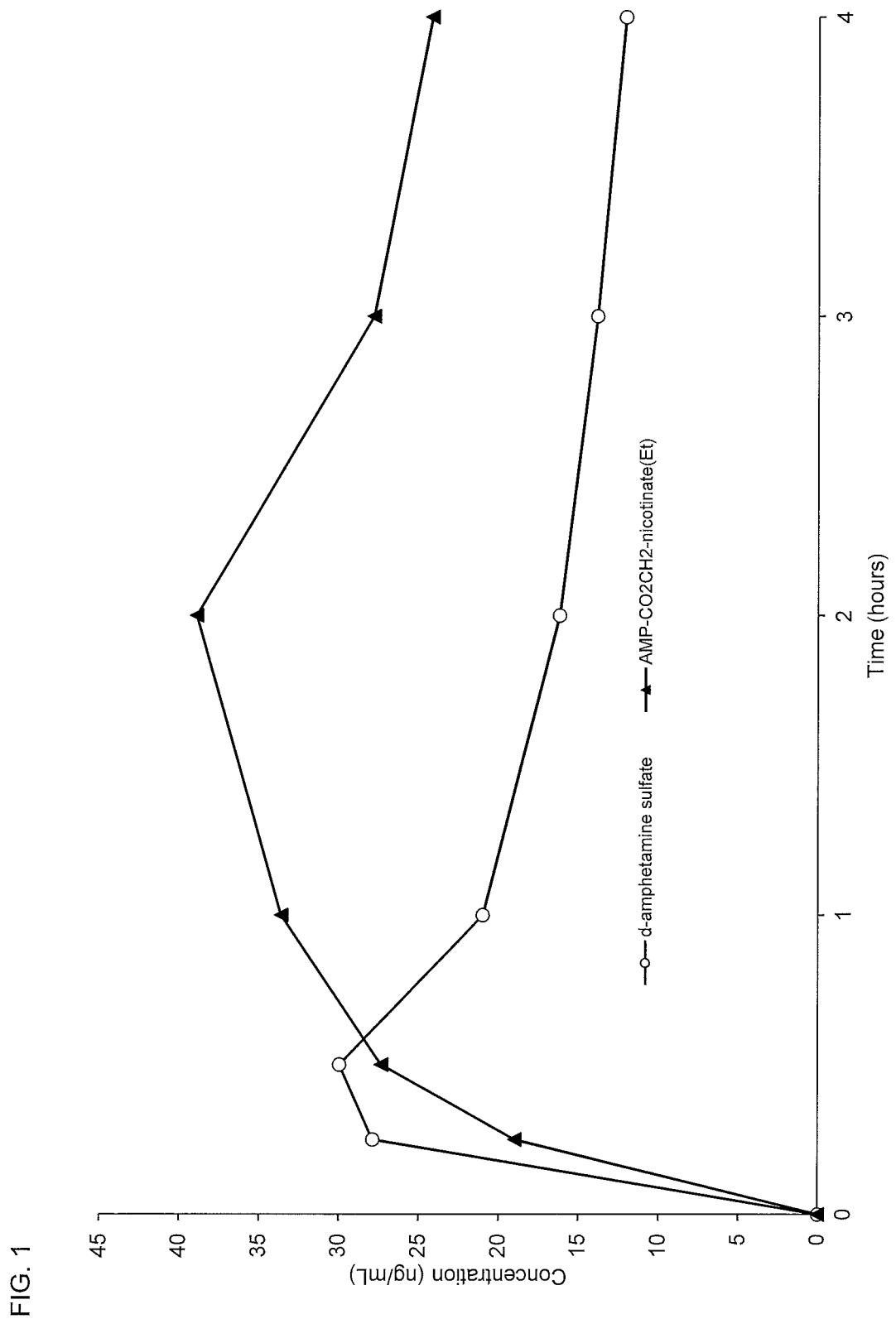
FIG. 1. Oral PK curves comparing d-amphetamine sulfate and d-amphetamine-$CO_2CH_2$-nicotinate ethyl ester (AMP-$CO_2CH_2$-nicotinate(Et)).
Figure 2:
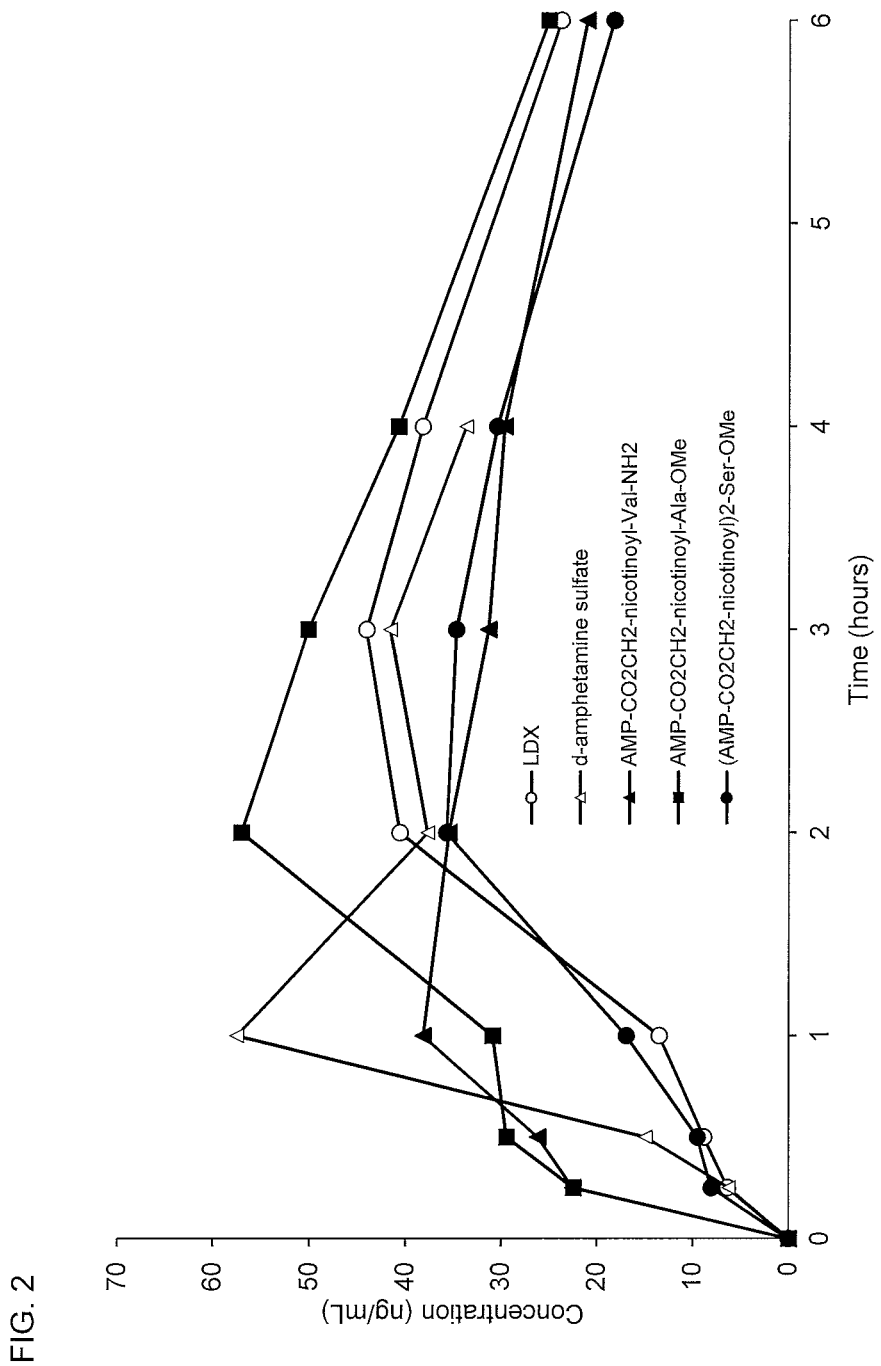
FIG. 2. Oral PK curves comparing lisdexamfetamine (LDX), d-amphetamine sulfate, d-amphetamine-$CO_2CH_2$-nicotinoyl-valinamide (AMP-$CO_2CH_2$-nicotinoyl-Val-$NH_2$), d-amphetamine-$CO_2CH_2$-nicotinoyl-alanine methyl ester (AMP-$CO_2CH_2$-nicotinoyl-Ala-OMe), and (d-amphetamine-$CO_2CH_2$-nicotinoyl)$_2$-serine methyl ester ((AMP-$CO_2CH_2$-nicotinoyl)$_2$-Ser-OMe).
Figure 3:
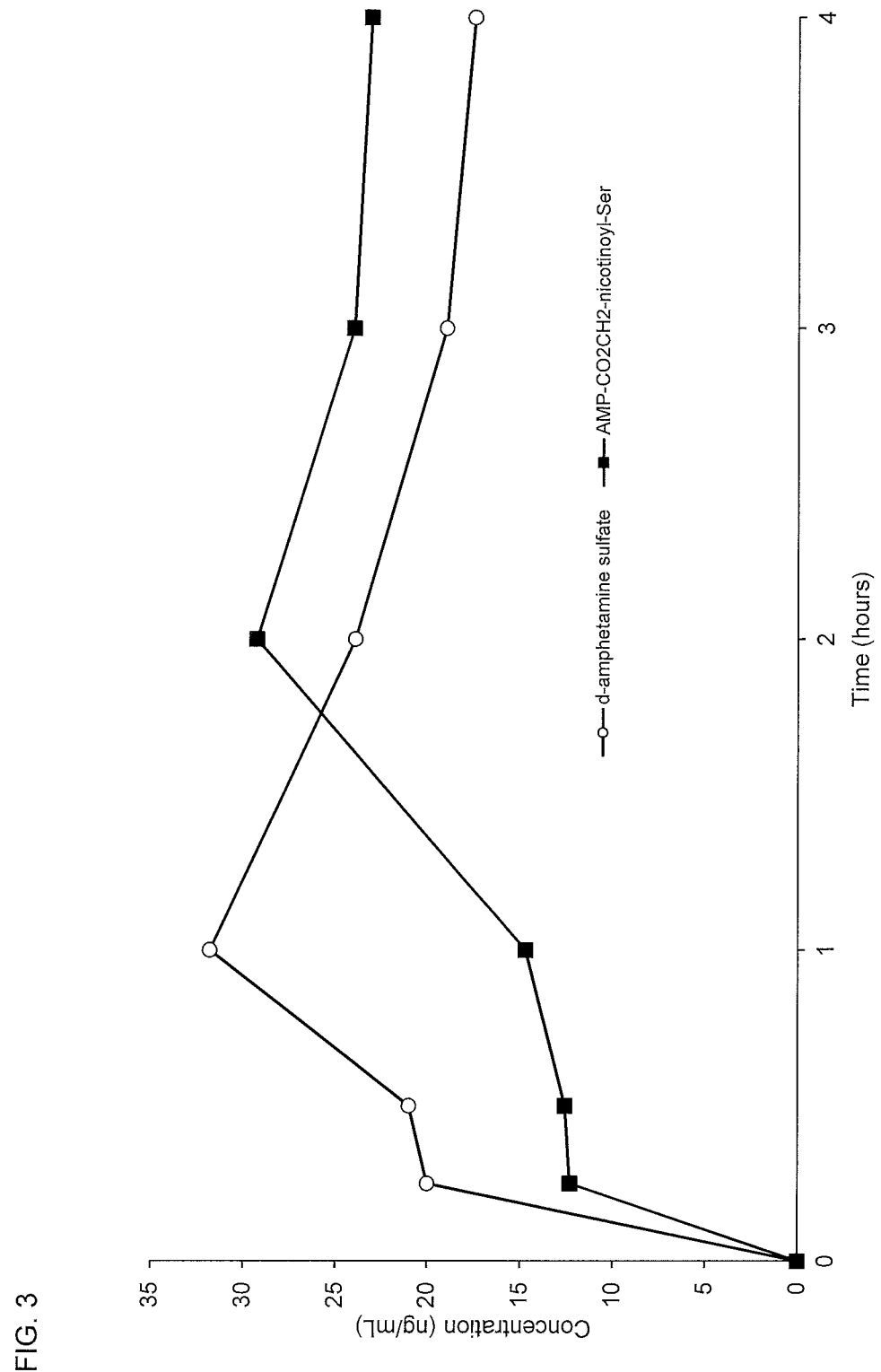
FIG. 3. Oral PK curves comparing d-amphetamine sulfate and d-amphetamine-$CO_2CH_2$-nicotinoyl-serine (AMP-$CO_2CH_2$-nicotinoyl-Ser).
Figure 4:
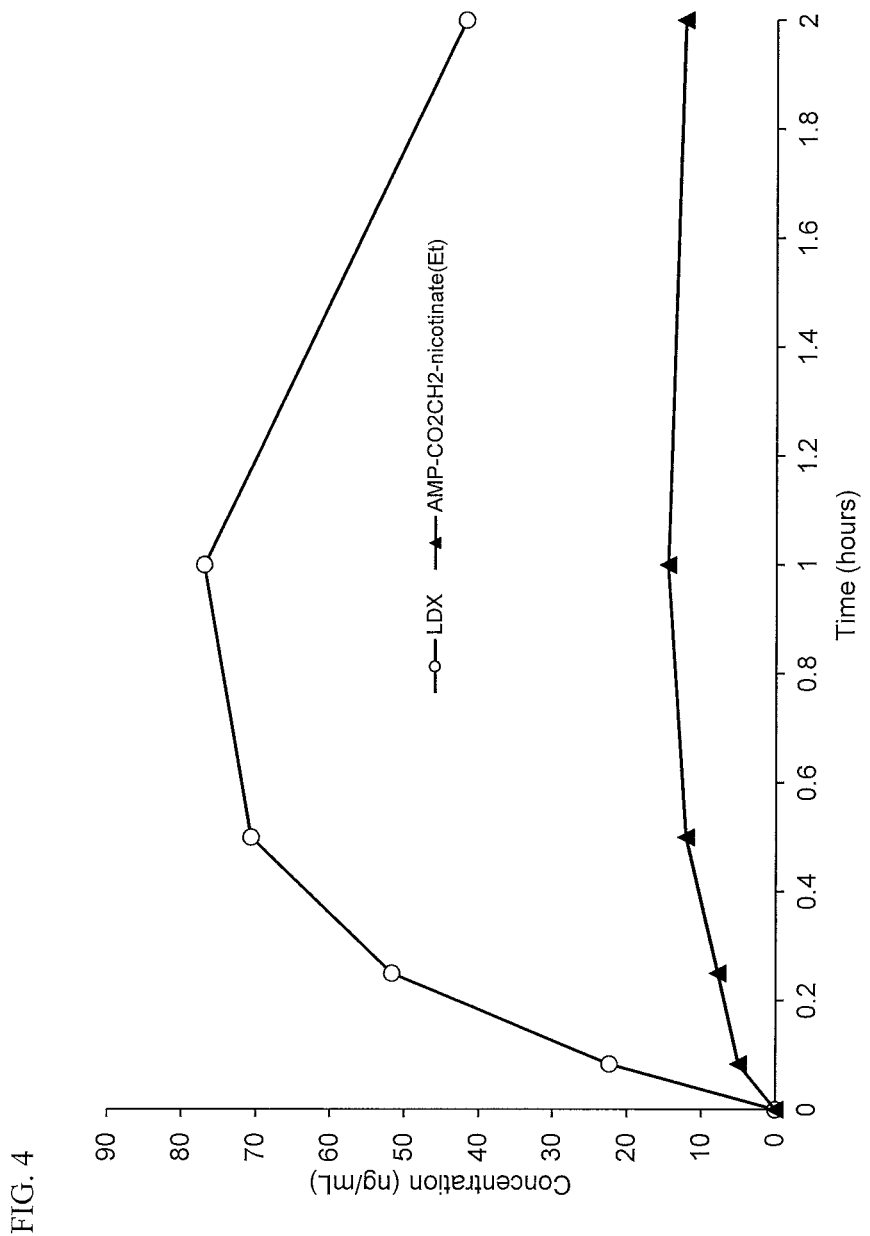
FIG. 4. Intravenous PK curves comparing lisdexamfetamine (LDX) and d-amphetamine-$CO_2CH_2$-nicotinate ethyl ester (AMP-$CO_2CH_2$-nicotinate(Et)).
Figure 5:
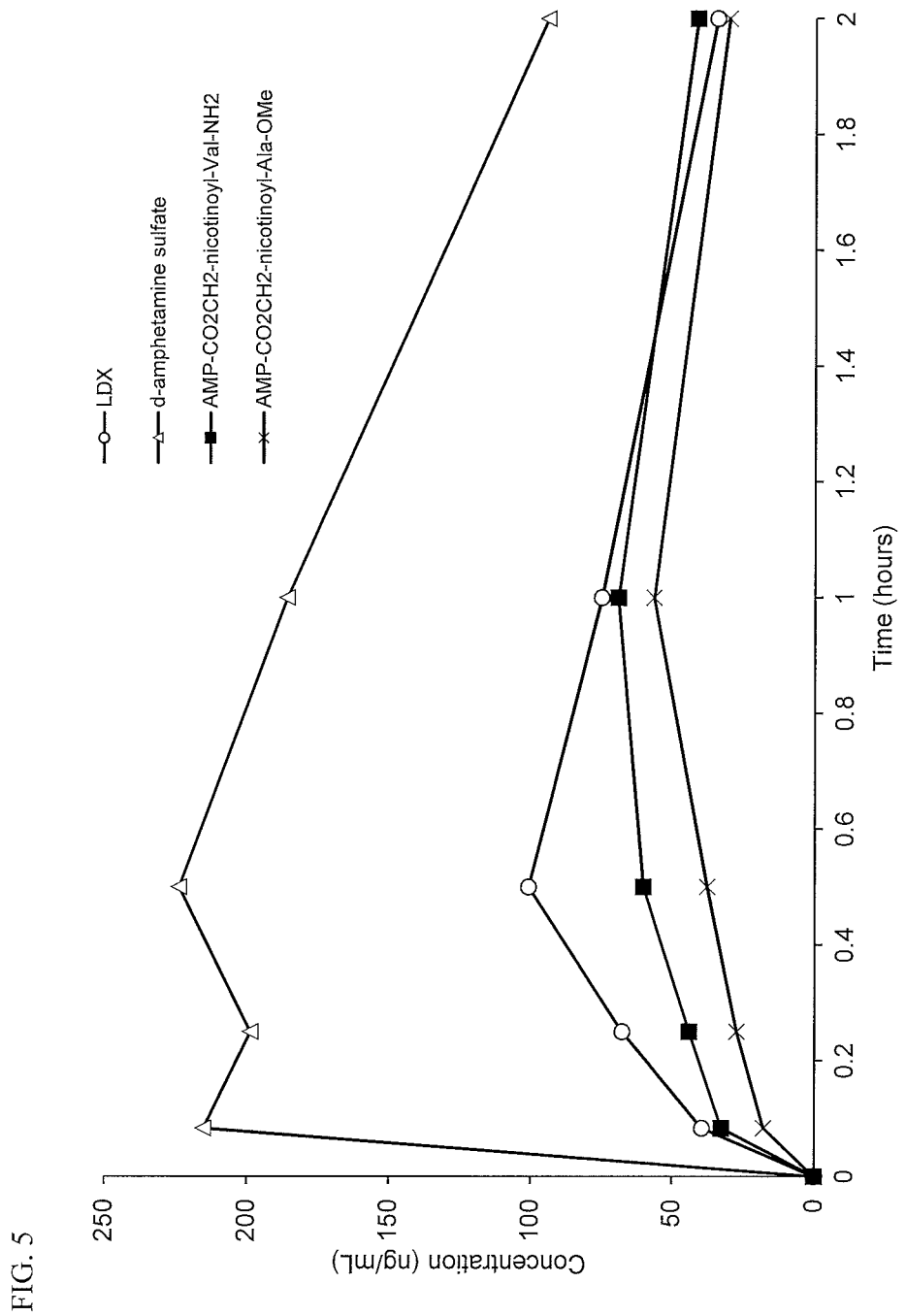
FIG. 5. Intravenous PK curves comparing lisdexamfetamine (LDX), d-amphetamine sulfate, d-amphetamine-$CO_2CH_2$-nicotinoyl-valinamide (AMP-$CO_2CH_2$-nicotinoyl-Val-$NH_2$), d-amphetamine-$CO_2CH_2$-nicotinoyl-alanine methyl ester (AMP-$CO_2CH_2$-nicotinoyl-Ala-OMe).
Figure 6:
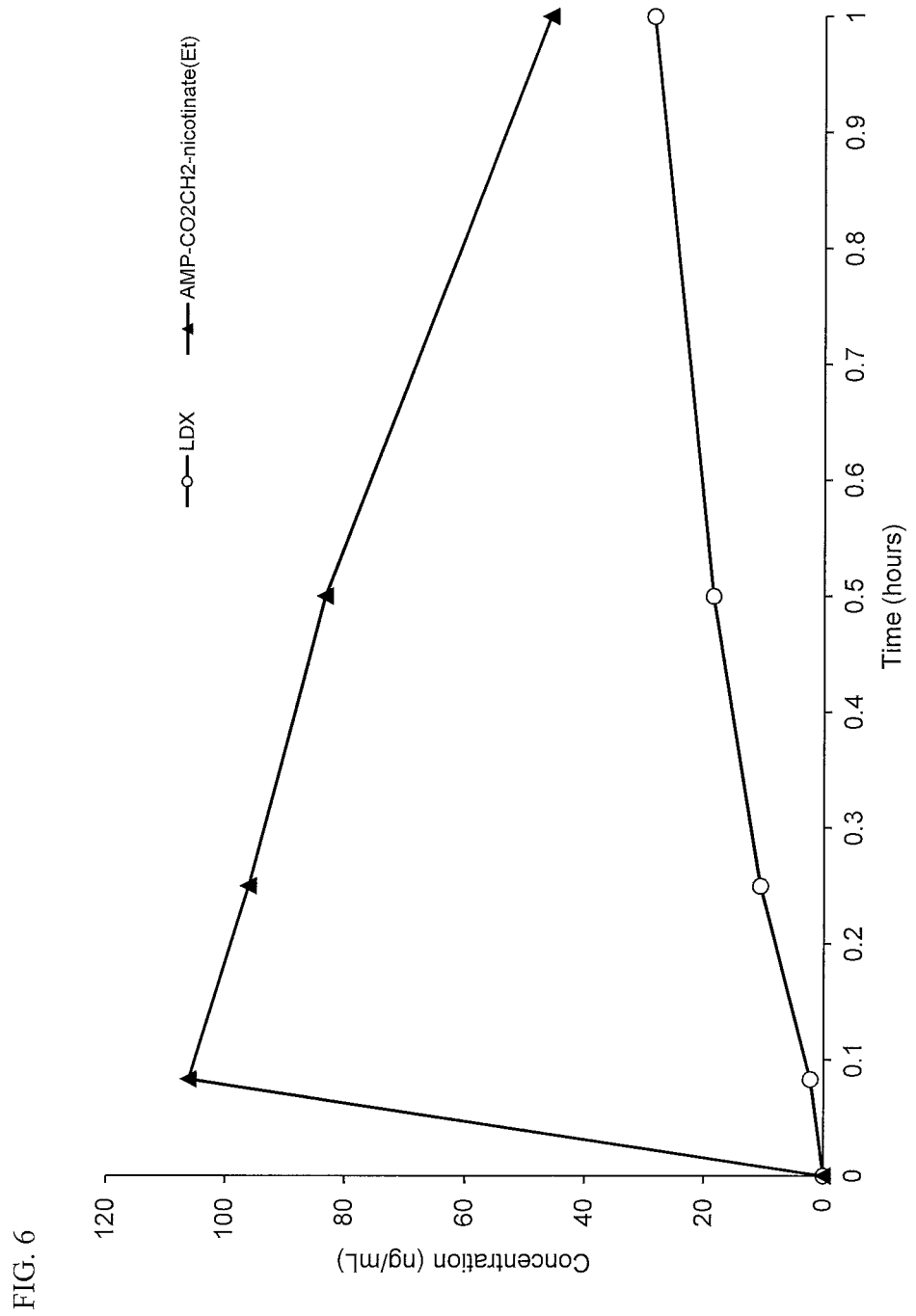
FIG. 6. Intranasal PK curves comparing lisdexamfetamine (LDX) and d-amphetamine-$CO_2CH_2$-nicotinate ethyl ester (AMP-$CO_2CH_2$-nicotinate(Et)).
Figure 7:
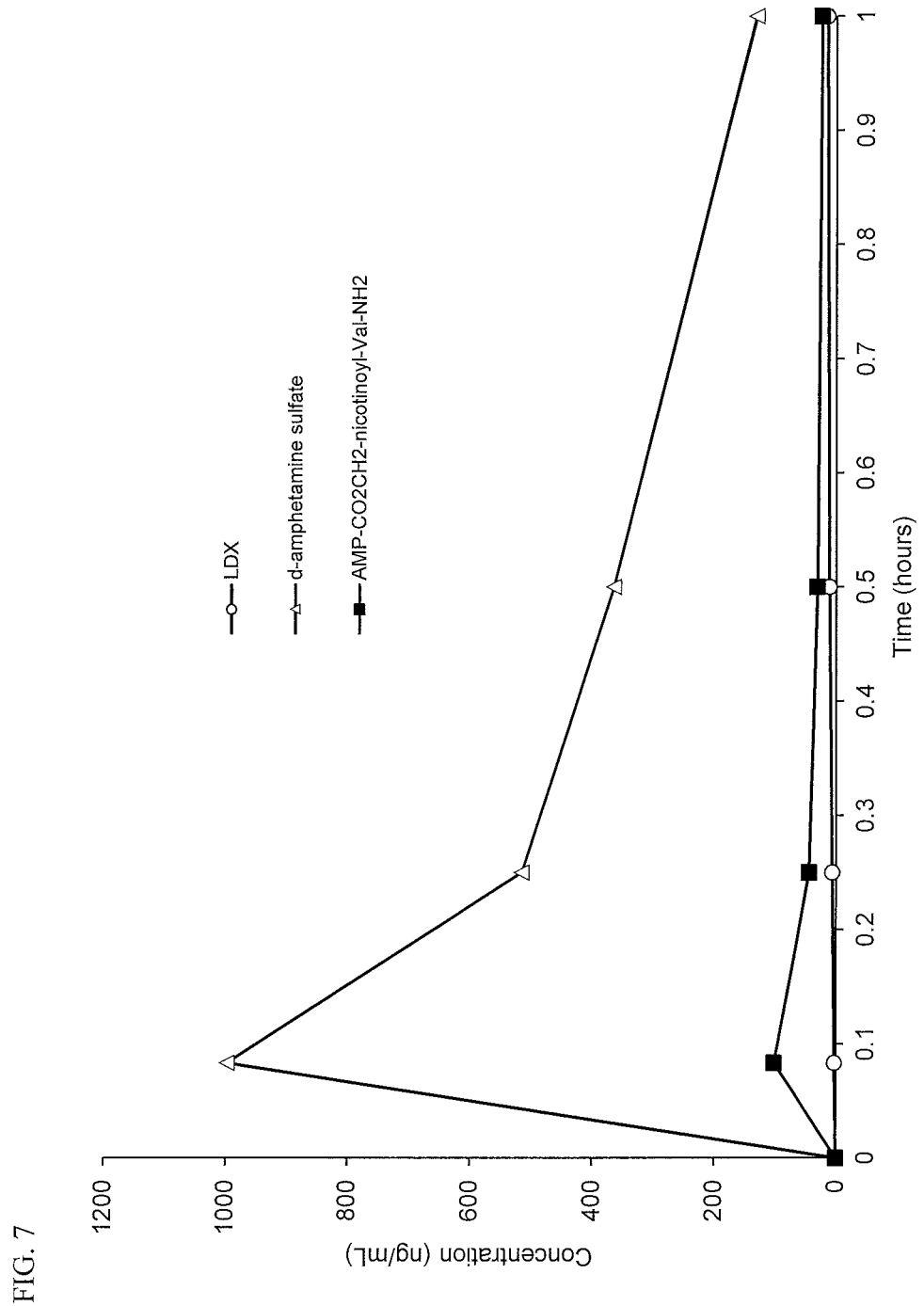
FIG. 7. Intranasal PK curves comparing lisdexamfetamine (LDX), d-amphetamine sulfate and d-amphetamine-$CO_2CH_2$-nicotinoyl-valinamide (AMP-$CO_2CH_2$-nicotinoyl-Val-$NH_2$).

The present technology describes, in general, novel compounds, and compositions of the stimulant d-amphetamine, salts thereof, other derivatives thereof, and combinations thereof. Additionally, the presently described technology also relates generally to the methods of making and using these new compounds, and compositions.

As used herein, an "amino acid" refers to a natural, standard, non-standard, unusual, synthetic, and/or essential amino acid, and can be an L-amino acid or a D-amino acid, or a combination thereof.

As used herein, "d-amphetamine" shall mean any of the sympathomimetic phenethylamine derivatives which have central nervous system stimulant activity, including, but not limited to, d-amphetamine (alpha-methyl-phenethylamine), methamphetamine, p-methoxyamphetamine, methylenedioxyamphetamine, 2,5-dimethoxy-4-methylamphetamine, 2,4,5-trimethoxyamphetamine, 3,4-methylenedioxy-methamphetamine, and methylphenidate.

As used herein, "in a manner inconsistent with the manufacturer's instructions" or similar expression is meant to include, but is not limited to, consuming amounts greater than amounts described on the label or ordered by a licensed physician, and/or altering by any means (e.g., crushing, breaking, melting, separating, etc.) the dosage formulation such that the composition may be injected, inhaled or smoked.

As used herein, the phrases such as "decreased," "reduced," "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

As used herein, the term "substance use disorders", or "stimulant use disorder" or the acronym "SUD", can be characterized as a maladaptive, narrowing of behaviors toward procurement and use of the drug of abuse at the expense of other, more constructive behaviors maintained by non-drug reinforcers. Success of any intervention can be measured, in part, by the extent to which it promotes a reallocation of behavior away from the drug of abuse or toward non-drug reinforcers that are generally deemed to be healthier. Pharmacotherapy, in particular agonist-like medications, have a number of properties that can promote such a behavioral reallocation.

As used herein, the term "agonist medications", or "agonist replacement therapies", are mechanistically similar to the abused drug in terms of receptor-mediated effects and pharmacodynamic effects but differ with respect to pharmacokinetic properties. Desirable attributes for an agonist replacement therapy include overlapping receptor pharmacology with the drug of abuse, oral bioavailability, slow onset of action, long duration of action.

In accordance with some aspects, the present technology provides amphetamine in a compound form. More specifically, the amphetamine comprises at least one organic compound covalently bonded or attached to amphetamine.

In some aspects, the compound has the structure of Formula IB:

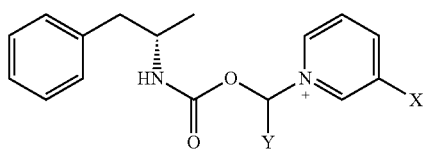

Formula IB where X is A-COO—R;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and
where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula ID

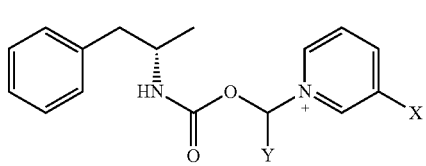

Formula ID where X is A-CO—NR$^1$R$^2$;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and
where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IIB:

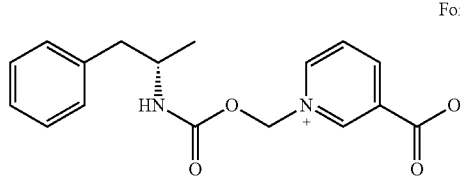

Formula IIB where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IID:

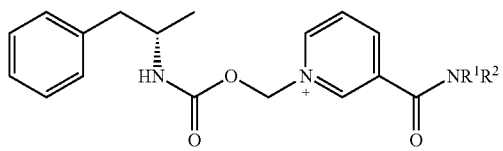

Formula IID where Y is hydrogen, A is absent, and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound is AMP-CO$_2$CH$_2$-nicotinate(Et) or pharmaceutical salt thereof having the following structure:

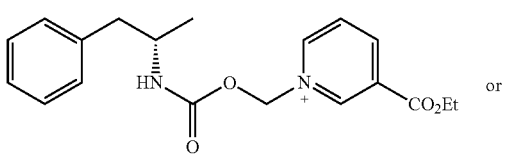

or

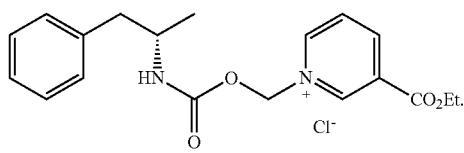

In some aspects, the compound is AMP-CO$_2$CH$_2$-nicotinoyl-Val-NH$_2$ or pharmaceutical salt thereof having the following structure:

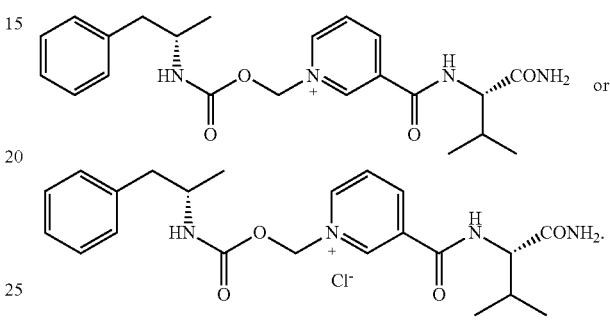

In some aspects, the compound is AMP-CO$_2$CH$_2$-nicotinoyl-Ser or pharmaceutically acceptable salt thereof having the following structure:

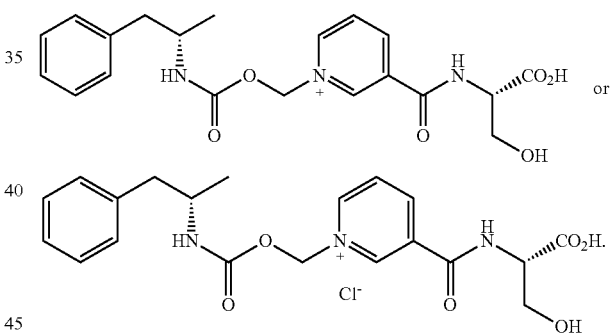

In some aspects, the compound is AMP-CO$_2$CH$_2$-nicotinoyl-Ala-OMe or pharmaceutically salt thereof having the following structure:

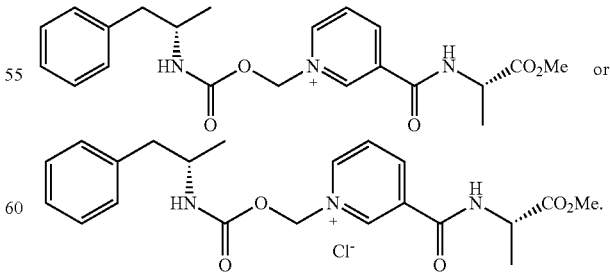

In some aspects, the compound is (AMP-CO$_2$CH$_2$-nicotinoyl)$_2$-Ser-OMe or a pharmaceutically acceptable salt thereof having the following structure:

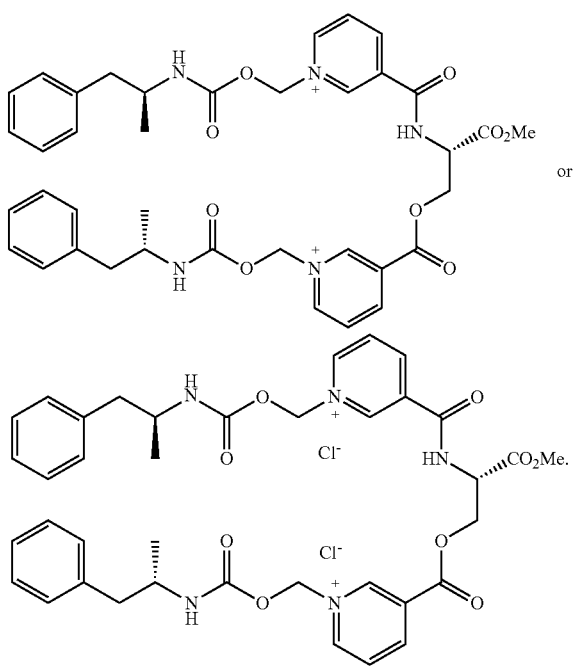

In some aspects, the pharmaceutically acceptable salt of the compound is a single salt or a mixed salt, where the one or more of the salts are selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In some aspects, the compound is a conjugate of d-amphetamine and has the structure of Formula IB:

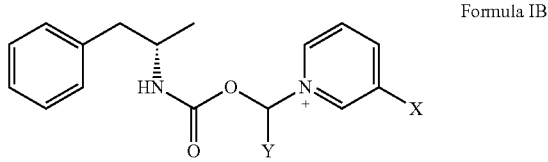

Formula IB where X is A-COO—R;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula ID

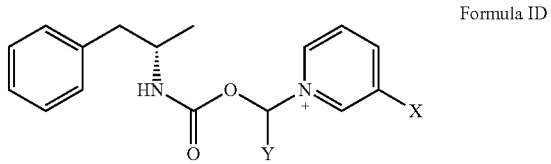

Formula ID where X is A-CO—NR$^1$R$^2$;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula IIB:

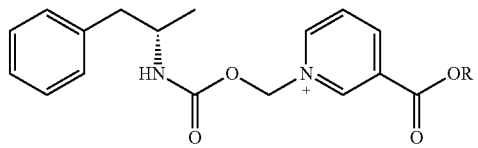

Formula IIB where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula IID:

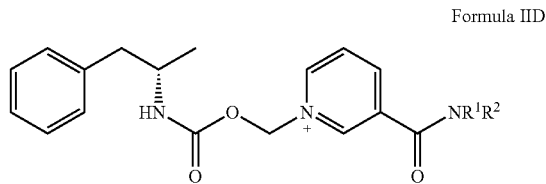

Formula IID where Y is hydrogen, A is absent, and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the conjugate is AMP-CO$_2$CH$_2$-nicotinate(Et) or pharmaceutical salt thereof having the following structure:

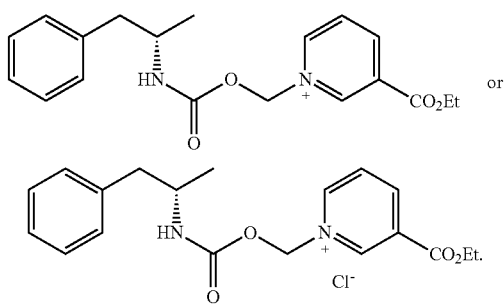

In some aspects, the conjugate is AMP-CO$_2$CH$_2$-nicotinoyl-Val-NH$_2$ or pharmaceutical salt thereof having the following structure:

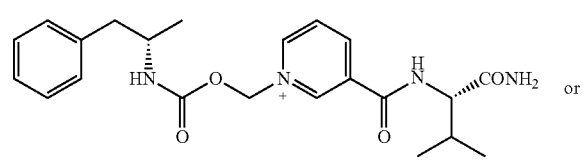

-continued

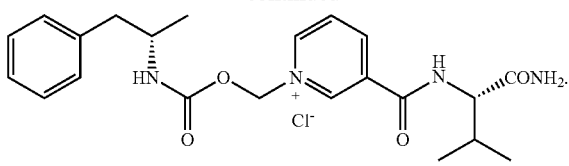

In some aspects, the conjugate is AMP-CO$_2$CH$_2$-nicotinoyl-Ser or pharmaceutically acceptable salt thereof having the following structure:

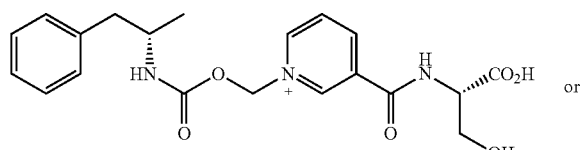

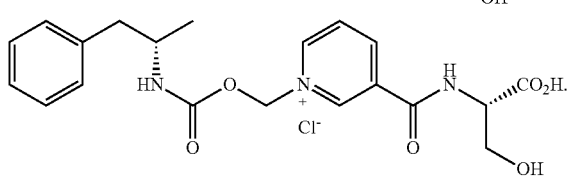

In some aspects, the conjugate is AMP-CO$_2$CH$_2$-nicotinoyl-Ala-OMe or pharmaceutically salt thereof having the following structure:

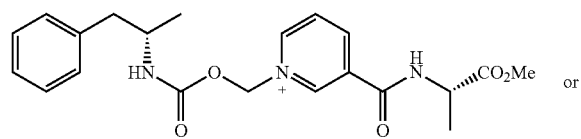

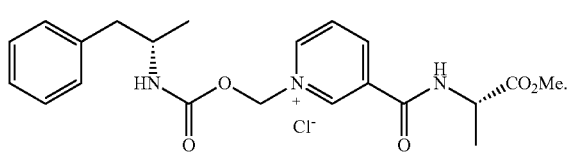

In some aspects, the conjugate is (AMP-CO$_2$CH$_2$-nicotinoyl)$_2$-Ser-OMe or a pharmaceutically acceptable salt thereof having the following structure:

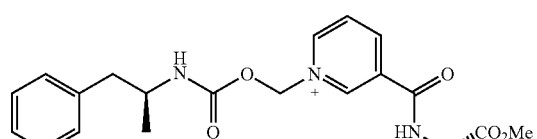

or

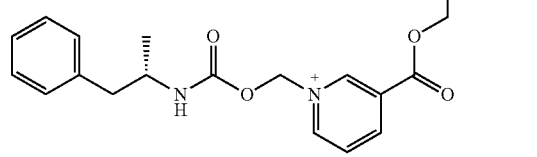

-continued

In some aspects, the pharmaceutically acceptable salt of the conjugate is a single salt or a mixed salt, where the one or more salts are selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In some aspects, the amphetamine portion of the conjugate can be d-amphetamine or l-amphetamine. In other aspects, the compositions of the present technology comprise a mixture of conjugates of d-amphetamine and conjugates of l-amphetamine. In further aspects, the mixture of conjugates may be a racemic mixture. It should be appreciated that portions of the conjugates other than amphetamine can also have chiral centers that create additional stereoisomers. The compositions of this technology can comprise single stereoisomers or any mixture of stereoisomers.

In some aspects, the X of the compound or the conjugate is located at the C-3 or C-5 position of the pyridine ring. It should be appreciated that for symmetry reasons C-3 is equivalent to C-5.

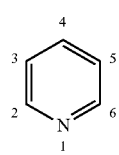

Pyridine

Some aspects are a composition comprising a conjugate of d-amphetamine. In some aspects, the composition is formulated for oral, suppository, powder for injection, intravenous, intranasal, or intrathecal administration. In yet another aspect, the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension. In yet another aspect, the composition further comprises one or more excipients, wherein the excipients are selected from the group consisting of antiadherents, binders, coatings, disintegrants, fillers, flavors, dyes, colors, glidants, lubricants, preservatives, sorbents, sweeteners, derivatives thereof, and combinations thereof. In yet a further aspect the binder is selected from the group consisting of hydroxypropylmethylcellulose, ethyl cellulose, povidone, acrylic and methacrylic acid co-polymers, pharmaceutical glaze, gums, gelatin, cellulose, cellulose derivatives, polyvinylpyrrolidone, starch, sucrose and polyethylene glycol, and milk derivatives.

In some aspects, the conjugate is present in an amount per unit dose of between about 0.1 mg and about 2000 mg per unit dose. In yet another aspect, the conjugate is present in an amount per unit dose of between about 0.1 mg and about 1000 mg per unit dose. In another aspect, the conjugate is present in an amount per unit dose of between about 0.5 mg and about 500 mg per unit dose. In a further aspect, the conjugate is present in an amount per unit dose of between about 1 mg and about 250 mg per unit dose. In yet another aspect, the conjugate is present in an amount per unit dose of between about 1.5 mg and about 100 mg per unit dose. In yet another aspect, the conjugate is present in an amount per unit dose of between about 0.5 mg and about 2000 mg per unit dose, alternatively about 1 mg and about 2000 mg per unit dose, alternatively about 2 mg and about 2000 mg per unit dose, alternatively about 5 mg and about 2000 mg per unit dose, alternatively about 10 mg and about 2000 mg per unit dose, alternatively about 20 mg and about 2000 mg per unit dose, alternatively about 40 mg and about 2000 mg per unit dose, alternatively about 80 mg and about 2000 mg per unit dose, alternatively about 160 mg and about 2000 mg per unit dose, alternatively about 320 mg and about 2000 mg per unit dose, alternatively about 640 mg and about 2000 mg per unit dose, alternatively about 1280 mg and about 2000 mg per unit dose, In yet another aspect, the conjugate is present in an amount per unit dose of between about 0.1 mg and 2000 mg per unit does, alternatively about 0.1 mg and about 1900 mg per unit dose, alternatively about 0.1 mg and about 1800 mg per unit dose, alternatively about 0.1 mg and about 1700 mg per unit dose, alternatively about 0.1 mg and about 1600 mg per unit dose, alternatively about 0.1 mg and about 1500 mg per unit dose, alternatively about 0.1 mg and about 1400 mg per unit dose, alternatively about 0.1 mg and about 1300 mg per unit dose, alternatively about 0.1 mg and about 1200 mg per unit dose, alternatively about 0.1 mg and about 1100 mg per unit dose, alternatively about 0.1 mg and about 1000 mg per unit dose, alternatively about 0.1 mg and about 900 mg per unit dose, alternatively about 0.1 mg and about 800 mg per unit dose, alternatively about 0.1 mg and about 700 mg per unit dose, alternatively about 0.1 mg and about 600 mg per unit dose, alternatively about 0.1 mg and about 500 mg per unit dose, alternatively about 0.1 mg and about 400 mg per unit dose, alternatively about 0.1 mg and about 300 mg per unit dose, alternatively about 0.1 mg and about 200 mg per unit dose, alternatively about 0.1 mg and about 100 mg per unit dose, alternatively about 0.1 mg and about 90 mg per unit dose, alternatively about 0.1 mg and about 80 mg per unit dose, alternatively about 0.1 mg and about 70 mg per unit dose, alternatively about 0.1 mg and about 60 mg per unit dose, alternatively about 0.1 mg and about 50 mg per unit dose, alternatively about 0.1 mg and about 40 mg per unit dose, alternatively about 0.1 mg and about 30 mg per unit dose, alternatively about 0.1 mg and about 20 mg per unit dose, alternatively about 0.1 mg and about 10 mg per unit dose, alternatively about 0.1 mg and about 5 mg per unit dose, and alternatively about 0.1 mg and about 1 mg per unit dose.

In some aspects the composition further comprises one or more additional pharmacological substance selected from the group consisting of stimulants, anti-depressants, combinations thereof and prodrugs thereof. In another aspect, the composition further comprises one of more of unconjugated amphetamine, unconjugated methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, or ziprasidone. In another aspect, the composition furthers comprises unconjugated amphetamine, an isomer thereof, or an amphetamine conjugate. In yet a further aspect, the isomer of unconjugated amphetamine is unconjugated d-amphetamine. In another aspect, the composition further comprises unconjugated methylphenidate, an isomer thereof, or a methylphenidate conjugate. In yet a further aspect, the isomer of unconjugated methylphenidate is unconjugated d-methylphenidate. In a further aspect, the conjugate of methylphenidate is serdexmethylphenidate.

In some aspects, the conjugate is provided in an amount sufficient to provide a similar or decreased AUC when compared to unconjugated d-amphetamine when orally administered at equimolar doses. In some aspects, the conjugate is provided in an amount sufficient to provide a similar or decreased $C_{max}$ as compared to unconjugated d-amphetamine when administered orally at equimolar doses. In yet another aspect, the conjugate is provided in an amount sufficient to provide a decreased $C_{max}$ and a similar or decreased AUC as compared to unconjugated d-amphetamine when administered orally at equimolar doses. In yet another aspect, intranasal or intravenous administration of the at least one conjugate provides a lower AUC and/or Cmax when compared to an equivalent molar amount of unconjugated d-amphetamine In another aspect, the composition comprising the conjugate is provided in an amount sufficient to provide a longer $T_{max}$ when compared to unconjugated d-amphetamine when administered orally at equimolar doses. In another aspect, the composition comprising the conjugate is provided in an amount sufficient to provide a similar $T_{max}$ when compared to unconjugated d-amphetamine when administered orally at equimolar doses.

In some aspects, the composition comprising the conjugate provides reduced abuse potential as compared to unconjugated d-amphetamine. In another aspect, the composition comprising the conjugate is provided in an amount sufficient to provide a longer $T_{max}$ when compared to unconjugated d-amphetamine when administered at equimolar doses. In another aspect, the composition comprising the conjugate is provided in an amount sufficient to provide a similar $T_{max}$ when compared to unconjugated d-amphetamine when administered at equimolar doses. In yet another aspect the composition comprising the conjugate has an improved safety profile when compared to unconjugated d-amphetamine. In some aspects, the composition comprising the conjugate produces reduced or insignificant pharmacological activity when administered by parenteral routes. In yet another aspect, the composition comprising the conjugate has a reduced plasma or blood concentration of released d-amphetamine when administered intranasally or intravenously as compared to unconjugated d-amphetamine when administered in equimolar amounts.

In some aspects, the composition comprising the conjugate provides a lower AUC and/or $C_{max}$ for d-amphetamine released from the conjugate when compared to an equivalent molar amount of unconjugated d-amphetamine following intravenous or intranasal administration of the composition to a subject. In another aspect, the composition comprising the conjugate provides a longer $T_{max}$ for d-amphetamine released from the conjugate when compared to an equivalent molar amount of unconjugated d-amphetamine following intravenous or intranasal administration of the composition to a subject. In some aspects, upon administration to a subject, the composition comprising the conjugate results in an extended release of d-amphetamine in the subject compared to the release of d-amphetamine upon administration of an equivalent molar amount of unconjugated d-amphetamine. In yet another aspect the composition comprising the conjugate exhibits less variability in inter-subject or intra-subject d-amphetamine plasma concentrations when compared to unconjugated d-amphetamine.

In some aspects, some compounds of the present invention containing an nicotinoyl moiety unexpectedly and non-obviously result in different and/or improved d-amphetamine exposure following oral, intranasal, and/or intravenous administration in a subject when compared to a compound of the same structure but with the nicotinoyl replaced by a isonicotinoyl moiety. In one aspect, d-amphetamine-$CO_2CH_2$-nicotinoyl-Val-$NH_2$ provides increased oral bioavailability of d-amphetamine compared to d-amphetamine-$CO_2CH_2$-isonicotinoyl-Val-$NH_2$. In another aspect, d-amphetamine-$CO_2CH_2$-nicotinate(Et) provides increased oral bioavailability of d-amphetamine compared to d-amphetamine-$CO_2CH_2$-isonicotinate(Et). In another aspect, AMP-$CO_2CH_2$-nicotinate(Et) decreases exposure to d-amphetamine after intravenous administration when compared to AMP-$CO_2CH_2$-isonicotinate(Et).

Another aspect of the present technology is a composition for treating a patient having a disorder or condition requiring stimulation of the central nervous system of the patient, wherein the composition has reduced abuse potential when administered compared to unconjugated d-amphetamine.

Another aspect of the present technology is a method of treating a patient having a disease, disorder or condition mediated by controlling, preventing, limiting, or inhibiting neurotransmitter uptake, the method comprising administering to a patient in need thereof a pharmaceutically effective amount of the composition comprising a conjugate of the current invention.

Another aspect of the present technology is a method of treating a patient having a disease, disorder or condition mediated by increasing neurotransmitter concentrations in the synapse, the method comprising administering to a patient in need thereof a pharmaceutically effective amount of the composition comprising a conjugate of the current invention.

Another aspect of the present technology is a method of treating a patient having a disorder or condition requiring stimulation of the central nervous system of the patient, the method comprising orally administering to a patient in need thereof a pharmaceutically effective amount of the composition comprising a conjugate of the current invention. In some aspects, the disease or condition is attention-deficit hyperactivity disorder, attention deficit disorder, autistic spectrum disorder, autism, Asperger's disorder, pervasive developmental disorder, sleep disorder, obesity, depression, bipolar disorder, eating disorder, binge eating, chronic fatigue syndrome, excessive daytime sleepiness, insomnia, schizophrenia, major depressive disorder, narcolepsy, postural orthostatic tachycardia syndrome, Tourette syndrome, nervous tics, substance use disorder, lethargy, depression, neural insult or obesity. In yet another aspect, the disease or condition is attention-deficit hyperactivity disorder. In yet another aspect, the disease or condition is Tourette syndrome or nervous tics.

As a person of ordinary skill in the art will understand, drug products are considered pharmaceutical equivalents if they contain the same active ingredient(s), are of the same dosage form, route of administration, and are identical in strength or concentration. Pharmaceutically equivalent drug products are formulated to contain the same amount of active ingredient in the same dosage form and to meet the same or compendial or other applicable standards (i.e., strength, quality, purity, and identity), but they may differ in characteristics such as shape, scoring configuration, release mechanisms, packaging, excipients (including colors, flavors, preservatives), expiration time, and, with certain limits, labeling. Drug products are considered to be therapeutic equivalents only if they are pharmaceutical equivalents and if they can be expected to have the same clinical effect and safety profile when administered to patients under the conditions specified in the labeling. The term "bioequivalent," on the other hand, describes pharmaceutical equivalent or pharmaceutical alternative products that display comparable bioavailability when studied under similar experimental conditions.

In accordance with the presently described technology, release of d-amphetamine after oral administration of the compounds of the presently described technology would occur under desired physiological conditions. Preferably, other routes of administration (e.g., intranasal or intravenous) do not break the compound down to any appreciable extent. In some aspects, reduction in d-amphetamine exposure following intranasal and/or intravenous administration is 50%, 30%, 20%, <10%, etc. of the exposure following intranasal and/or intravenous administration of an equimolar dose of unconjugated d-amphetamine. Also, preferably certain compounds or aspects of the present invention will resist release of amphetamine via external means (chemical, enzymatic, or other) The breakdown ratio of the compound that can be achieved through external means is preferably less than about 50%, alternatively less than about 25%, alternatively less than about 20%, alternatively less than about 10%.

Embodiments of the compounds, compositions, and methods of the presently described technology are also believed to provide reduced potential for rebound, reduced potential for abuse or addiction, and/or improve d-amphetamine's stimulant related toxicities.

The d-amphetamine compounds of the presently described technology could be used for any condition requiring the stimulation of the central nervous system (CNS). These conditions include, for example, attention deficit hyperactivity disorder (ADHD), attention deficit disorder (ADD), obesity, narcolepsy, appetite suppressant, depression, anxiety, and wakefulness. D-amphetamine stimulants have also demonstrated usefulness in treating stimulant (e.g., cocaine, methamphetamine) abuse and addiction.

D-amphetamine stimulants have also been used extensively to improve battlefield alertness and to combat fatigue.

Therefore, in accordance with some aspects, the presently described technology provides d-amphetamine compositions comprising at least one d-amphetamine compound of the present technology.

One aspect is a composition that can prevent behavioral deterioration caused by d-amphetamine dosing, comprising the d-amphetamine compound of the present technology.

Another aspect is a composition that allows for lower doses of an active pharmaceutical ingredient comprising the d-amphetamine compound of the present technology.

Other formulations according to one or more aspects of the present technology may further comprise pharmaceutical additives including, but not limited to, lubricants such as magnesium stearate, calcium stearate, zinc stearate, powdered stearic acid, hydrogenated vegetable oils, talc, polyethylene glycol, and mineral oil; colorants such as Emerald Green Lake, FD&C Red No. 40, FD&C Yellow No. 6, D&C Yellow No. 10, or FD&C Blue No. 1 and other various certified color additives (See 21 CFR, Part 74); binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quaternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art.

The d-amphetamine compositions of the present technology may be manufactured according to any appropriate method known to those of skill in the art of pharmaceutical manufacture.

It should be noted that the above additives are not required for the d-amphetamine composition of the present technology to have sustained release in vivo properties. The d-amphetamine compounds of the present technology are chemically stable to prevent tampering or removing the d-amphetamine prior to oral ingestion. Also, the controlled release of d-amphetamine through oral administration of the d-amphetamine compound of the present technology is a designed property of the molecule and not related to the formulation. Therefore, the compound of the present technology can be easily formulated to different dosage forms. In one or more aspects of the present technology, no further sustained release additives are required to achieve a blunted or reduced pharmacokinetic curve (e.g., reduced euphoric effect) while achieving therapeutically effective amounts of d-amphetamine release when taken orally.

The compounds and compositions of the presently described technology can be formulated into and administered by a variety of dosage forms through any oral routes of delivery. Once administered, the compound will release d-amphetamine under digestive conditions. Any biologically-acceptable dosage form known to persons of ordinary skill in the art, and combinations thereof, are contemplated. Examples of preferred dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, oral films (e.g., fast dissolving thin strips), and combinations thereof.

Formulations of the present technology suitable for oral administration can be presented as discrete units, such as capsules, caplets, tablets, or oral films. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow.

If the capsule form is chosen, for example, excipients used in the capsule formulation could be broken up into four separate groups: bulk agent/binder, disintegrant, lubricant, and carrier. Soft gel or soft gelatin capsules may be prepared, for example, by dispersing the formulation of the present technology in an appropriate vehicle (vegetable oils are commonly used) to form a high viscosity mixture. This mixture can then be encapsulated with a gelatin-based film using technology and machinery known to those in the soft gel industry. The industrial units so formed are then dried to constant weight.

Chewable tablets, for example, may be prepared by mixing the formulations of the present technology with excipients designed to form a relatively soft, flavored, tablet dosage form that is intended to be chewed rather than swallowed. Conventional tablet machinery and procedures that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example, may be prepared by coating tablets using techniques such as rotating pan coating methods or air suspension methods to deposit a contiguous film layer on a tablet.

Compressed tablets, for example, may be prepared by mixing the formulation of the present technology with excipients intended to add binding qualities to disintegration qualities. The mixture can be either directly compressed or granulated then compressed using methods and machinery known to those in the industry. The resultant compressed tablet dosage units are then packaged according to market need, i.e., unit dose, rolls, bulk bottles, blister packs, etc.

Methods and other ingredients needed to make oral films or thin strips are known in the art. Potential film forming agents include pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, Arabic gum, polyacrylic acid, amylase, starch, dextrin, pectin, chitin, chitosan, levan, elsinan, collagen, gelatin, zein, gluten, soy protein isolate, whey protein isolate, casein, and mixtures thereof.

Also, saliva stimulating agents, plasticizing agents, cooling agents, surfactants, emulsifying agents, thickening agents, binding agents sweeteners, flavoring, coloring agents, preservatives, or taste masking resins may be employed in the oral films or thin strips. Preferred agents include pullulan, triethanol amine stearate, methyl cellulose, starch, triacetin, Polysorbate 80, xanthan gum, maltitol, sorbitol, and glycerol.

The presently described technology also contemplates the use of biologically-acceptable carriers which may be prepared from a wide range of materials. Without being limited thereto, such materials include diluents, binders, and adhesives, lubricants, plasticizers, disintegrants, colorants, bulking substances, sweeteners, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate, and castor oil are used to delay the release of water-soluble vitamins, such as vitamin $B_6$ and vitamin C In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of the present technology can include other suitable agents such as flavoring agents, preservatives and antioxidants. Such antioxidants would be food acceptable and could include, for example, vitamin E, carotene, BHT or other antioxidants known to those of skill in the art.

Other compounds which may be included are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. The suspensions and the emulsions may contain a carrier, for example, a natural gum, agar, sodium alginate, pectin, methylcellulose, carboxymethylcellulose or polyvinyl alcohol.

The dose range for adult human beings will depend on a number of factors including the age, weight, and condition of the patient. Suitable oral dosages of the compositions of the presently described technology can be the equivalents of those typically found in d-amphetamine treatments. Typical dosages for d-amphetamine salts can range from about 1 mg to about 500 mg, alternatively from about 1 mg to about 400 mg, alternatively from about 1 mg to about 300 mg, alternatively from about 1 mg to about 200 mg, alternatively from about 1 mg to about 100 mg, although higher dosages may be approved at later dates.

Tablets, capsules, oral films, and other forms of presentation provided in discrete units conveniently contain a daily dose, or an appropriate fraction thereof, of one or more of the compounds of the invention.

It is also possible for the dosage form of the present technology to combine any forms of release known to persons of ordinary skill in the art. These conventional release forms include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof are known in the art.

Compositions of the present technology may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the present technology may be provided in a blister pack or other such pharmaceutical package. Further, the compositions of the present technology may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the present technology can be demonstrated using standard pharmacological models that are known in the art. Furthermore, it will be appreciated that the compositions of the present technology can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In one or more aspects of the present technology, the solubility and dissolution rate of the composition can be substantially changed under different physiological conditions encountered, for example, in the intestine, at mucosal surfaces, or in the bloodstream. In one or more aspects of the present technology, the solubility and dissolution rate of the composition can substantially decrease the bioavailability of the d-amphetamine, particularly at doses above those intended for therapy. In one aspect of the present technology, the decrease in bioavailability occurs upon intranasal administration. In another aspect, the decrease in bioavailability occurs upon intravenous administration.

The presently described technology further provides methods for altering and/or delivering amphetamines in a manner that can decrease their potential for abuse.

One aspect provides a method for preventing behavioral deterioration or the rebound effect by administering to a patient in need of a d-amphetamine composition of the present technology.

Another aspect of the present technology is a method for reducing or preventing abuse of d-amphetamine comprising providing, administering, consuming, or prescribing a composition to a patient in need thereof, wherein said composition comprises a d-amphetamine compound of the present invention such that the pharmacological activity of d-amphetamine is decreased when the composition is used in a manner inconsistent with the manufacturer's instructions.

Another aspect of the present technology is a method of preventing behavioral deterioration or the rebound effect of d-amphetamine or stimulant treatment comprising providing, administering, consuming, or prescribing an d-amphetamine composition of the presently described technology to a patient in need thereof, wherein said composition comprises a d-amphetamine compound of the present invention that can decrease the potential of behavioral deterioration or the rebound effect from d-amphetamine or stimulant treatment.

Another aspect of the present technology is any of the preceding methods wherein the d-amphetamine composition used is adapted for oral administration, and wherein the d-amphetamine is resistant to release d-amphetamine from the organic acid moiety when the composition is administered parenterally, such as intranasally or intravenously.

Another aspect of the present technology provides methods of treating various diseases or conditions requiring the stimulation of the central nervous system (CNS) comprising administering compounds or compositions of the present technology which, optionally, further comprise commonly prescribed active agents for the respective illness or disease.

In one aspect, the composition comprising a d-amphetamine compound, a salt thereof, or a combination thereof provides immediate and extended release PK profiles when compared to unconjugated d-amphetamine.

A further aspect of the present technology is a kit comprising individual doses of a therapeutically effective amount of a composition comprising a d-amphetamine compound, conjugate, a salt thereof, or a combination thereof. In some aspects, the kit is in a unit dose pack.

In one aspect of the present invention, the amphetamine conjugates, compounds, and/or compositions have increased d-amphetamine plasma concentration compared to lisdexamfetamine dimesylate (or alternatively amphetamine sulfate) following oral administration for at least 1 hour, or at least 2 hours, or at least 4 or at least 6 hours. In other aspects of present invention, the amphetamine conjugates, compounds, and/or composition have decreased d-amphetamine plasma concentrations compared to d-amphetamine sulfate and similar d-amphetamine plasma concentrations compared to lisdexamfetamine dimesylate following oral administration for at least 1 hour, or at least 2 hours, or at least 4 hours, or at least 6 hours. In another aspect of the present invention, the amphetamine conjugates, compounds, and/or compositions thereof the present invention have decreased d-amphetamine plasma concentrations following intravenous or intranasal administration compared to lisdexamfetamine dimesylate or amphetamine sulfate for at least 1 hour, or at least 2 hours, or at least 4 hours, or at least 6 hours.

The presently described technology and its advantages will be better understood by reference to the following examples and/or schemes. These examples and/or schemes are provided to describe specific aspects of the present technology. By providing these specific examples and/or schemes, the applicants do not limit the scope and spirit of the present technology.

General Synthetic Procedure:

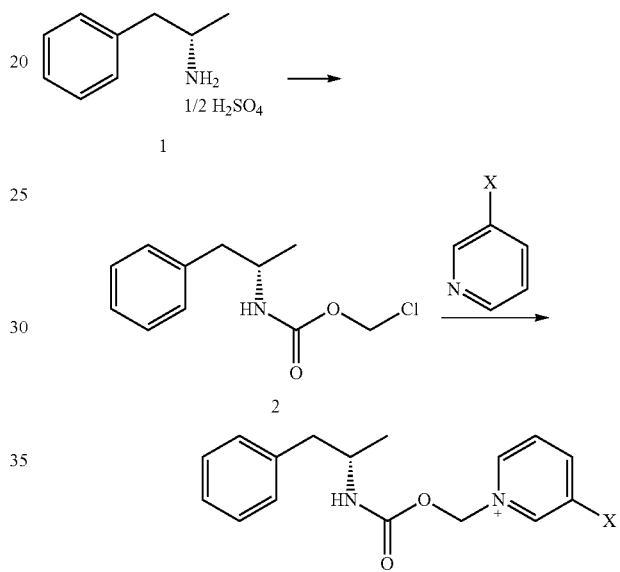

Amphetamine hemisulfate 1 was converted to chloromethyl carbamate 2 by adding chloromethyl chloroformate. The chloromethyl carbamate of amphetamine 2 and the respective pyridine derivative were heated in acetone or acetonitrile with or without NaI to give the amphetamine conjugate. A subsequent deprotection may be required if applicable.

Specific Procedures:

Synthesis of AMP-CO$_2$—CH$_2$-nicotinate(Et) 3f:

TABLE 1

Structure of conjugate 3f

| Comp | Structure |
|---|---|
| 3f | 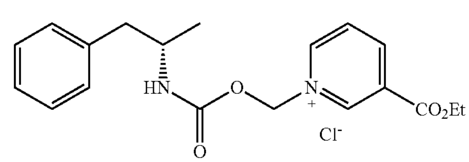 |

Synthetic Scheme for AMP-CO$_2$—CH$_2$-nicotinate(Et) 3f:

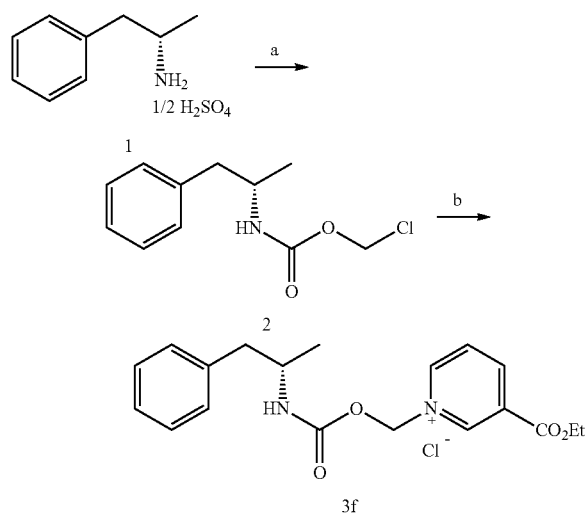

Step 1: Chloromethyl Carbamate of Amphetamine, ClCH$_2$OCO-AMP 2:

D-Amphetamine hemisulfate (4.640 g, 25.18 mmol) in DCM (80 mL) was cooled in ice-water bath. DIPEA (8.136 g, 62.95 mmol) was added. Then chloromethyl chloroformate (4.221 g, 32.74 mmol) in DCM (20 mL) was added over 15 min. The reaction was warmed up to room temperature over 30 min, then stirred for another 1.5 hr. Then, 5% of aq. NH$_4$Cl (40 mL) was added to quench the reaction. The DCM layer was separated and dried over sodium sulfate. The solvent was evaporated. The residue was purified by silica gel column chromatography (hexanes: ethyl acetate, 4:1) to give 4.9 g of 2 as syrup, which solidified when stored in the freezer. The yield was 85.5%.

Step 2: AMP-CO$_2$CH$_2$-nicotinate(Et) 3f:

The chloromethyl carbamate of amphetamine 2 (0.228 g, 1 mmol) and ethyl nicotinate in acetonitrile (8 mL) were heated at 80-85° C. for 8 hr. The solvent was evaporated. The residue was dissolved in DCM (1 mL). Then TBME (15 mL) and hexanes (15 m) was added. The upper layer was decanted. The remaining syrup was treated using the above procedure 3 more times, then was dried over vacuum to give 0.230 g of an amorphous solid. The yield was 60.7%.

Synthesis of Conjugates AMP-CO$_2$CH$_2$-3-(3-pyridyl)alanine 5z and AMP-CO$_2$CH$_2$-nicotinoyl-amino acid 6a-c:

TABLE 2

Structure of conjugate 5z

| Comp. | Structure |
|---|---|
| 5z | 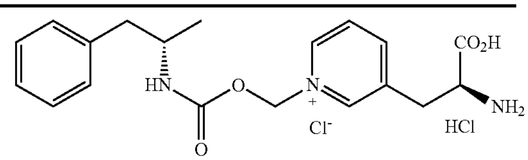 |

TABLE 3

Structures of conjugates 6a-6c

| Comp. | Structure |
|---|---|
| 6a | (pyridinium-methyl ester linked to phenylalanine-derived carbamate, coupled via amide to valine; Cl⁻ counterion) |
| 6b | (pyridinium-methyl ester linked to phenylalanine-derived carbamate, coupled via amide to alanine; Cl⁻ counterion) |
| 6c | (pyridinium-methyl ester linked to phenylalanine-derived carbamate, coupled via amide to serine; Cl⁻ counterion) |

Synthetic Scheme for AMP-CO$_2$CH$_2$-3-(3-pyridyl)alanine 5z:

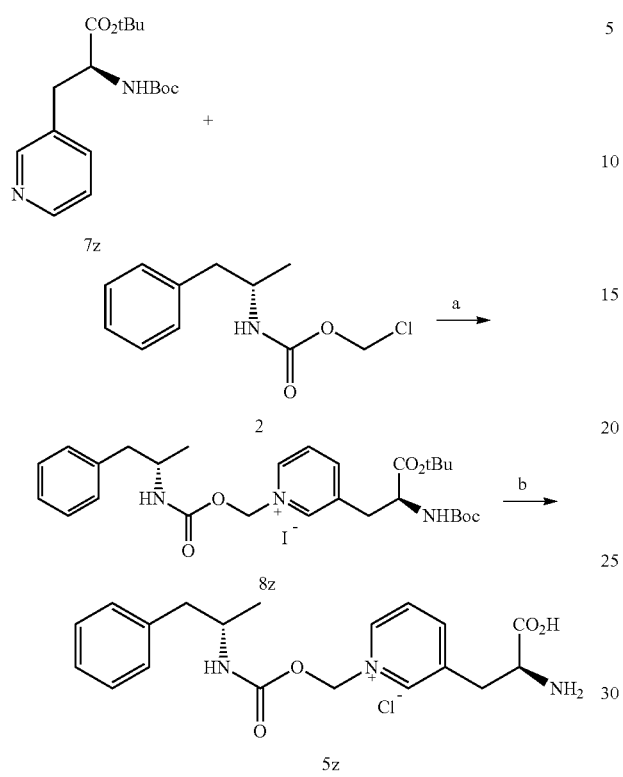

3-(3-pyridyl)-Boc-alanine tert-butyl ester 7z (0.226 g, 0.7 mmol), ClCH$_2$OCO-AMP 2 (0.180 g, 0.791 mmol) and NaI (0.111 g, 0.742 mmol) in acetonitrile (10 mL) were refluxed for 1 hr. The solid was filtered off. The filtrate was concentrated and dried over vacuum to give an amorphous solid. The solid in 4 M HCl/dioxane (10 mL) was stirred at room temperature for 12 hr. Solvent was evaporated to dryness and dried over vacuum to give an amorphous solid, which was dissolved in 8 mL of ethanol and treated with Dowex 1×8 twice (200-400, Cl form, 1 g and 0.5 g). The filtrate, after resin treatment, was concentrated and dried over vacuum to give 0.285 g of 5z as an amorphous solid. The yield was 94%.

Synthetic Scheme for Conjugates AMP-CO$_2$CH$_2$-nicotinoyl-valine 6a:

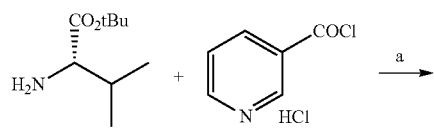

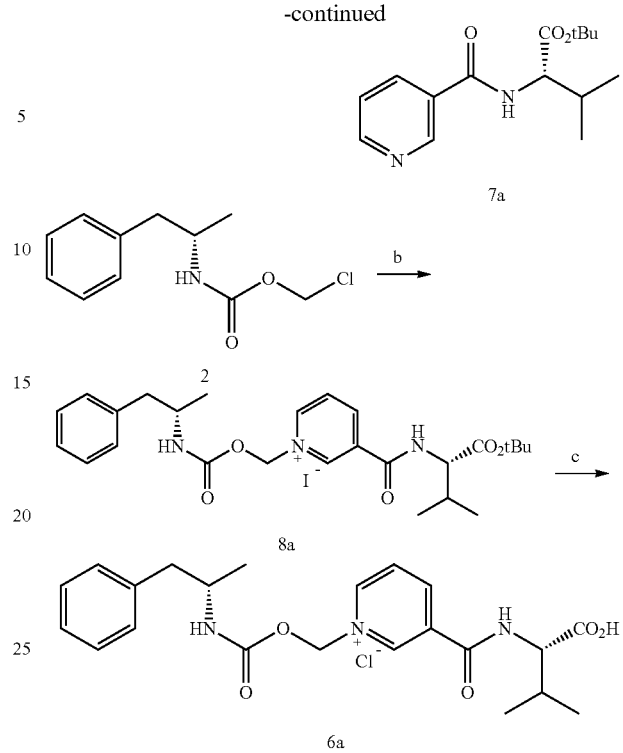

Step 1: Nicotinoyl-Val-OtBu 7a:

To valine t-butyl ester HCl salt (H-Val-OtBu HCl, 0.629 g, 3 mmol) in DCM (30 mL) was added Et$_3$N (1.25 ml, 9 mmol). Nicotinoyl chloride hydrochloride (0.534 g, 3 mmol) was added in 4 portions over 15 min in a water bath (room temperature). The reaction was stirred for 2 hr. Subsequently, 5% of aq. NH$_4$Cl (20 mL) was added to quench the reaction. The DCM layer was dried over Na$_2$SO$_4$. The product was purified by silica gel column chromatography (3% MeOH/DCM). 0.822 g of 7a was obtained as syrup. The yield was 98%.

Step 2: AMP-CO$_2$CH$_2$-nicotinoyl-Val 6a:

Nicotinoyl-Val-OtBu 7a (0.31 g, 1.11 mmol), ClCH$_2$OCO-AMP 2 (0.291 g, 1.28 mmol) and NaI (0.176 g, 1.18 mmol) in acetonitrile (10 mL) were refluxed for 1.5 hr. The solid was filtered off. The filtrate was concentrated to give an amorphous solid. To this solid was added 4 M HCl/dioxane (8 mL) and the mixture was stirred at room temperature for 3 hr. Solvent was evaporated to dryness and dried over vacuum for 1 hr. The resulting residue was dissolved in 8 mL of ethanol and treated with Dowex 1×8 twice (200-400, Cl form, 1 g and 0.5 g). The filtrate, after resin treatment, was concentrated and dried over vacuum to give 0.461 g of 6a as an amorphous solid. The yield was 93%.

Conjugates 6b and 6c were synthesized by similar procedures as 6a.

Synthesis of Conjugates AMP-CO$_2$CH$_2$-nicotinoyl-amino acid esters 9i-9n:

TABLE 4
Structures of conjugates 9i-9n
| Comp. | Structure | Comp. | Structure |
|---|---|---|---|
| 9i | 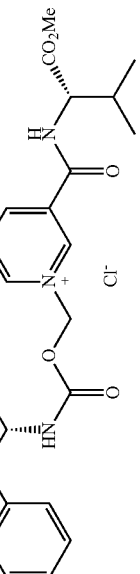 | 9j | 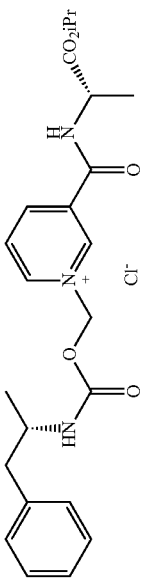 |
| 9k | 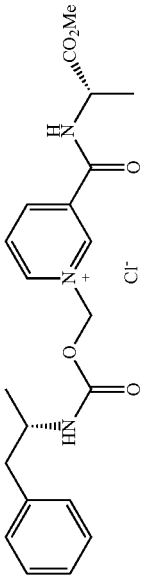 | 9l | 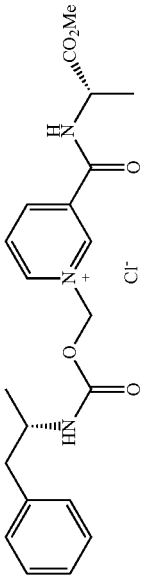 |
| 9m | 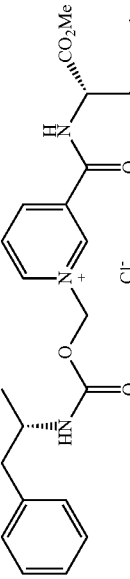 | 9n | 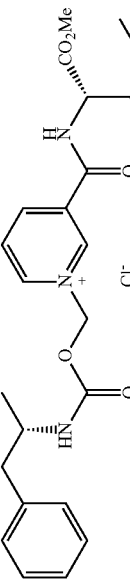 |

Synthetic scheme for Conjugates AMP-CO$_2$CH$_2$-nicotinoyl-amino acid esters 9i-9n:

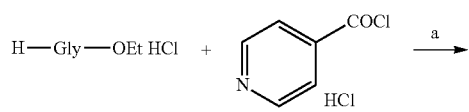

ness. The residue was dissolved in DCM (1.5 mL) and TBME (25 mL) was added. The upper layer was decanted. The remaining solid was dissolved in DCM (15 ml) and concentrated to give solid. After drying over vacuum, 0.314 g of 9i was obtained. The yield was 90%.

Conjugates 9j-9n were synthesized by procedures similar to 9i.

Synthesis of Conjugates AMP-CO$_2$CH$_2$-nicotinoyl-amino acid amide 11c:

TABLE 5

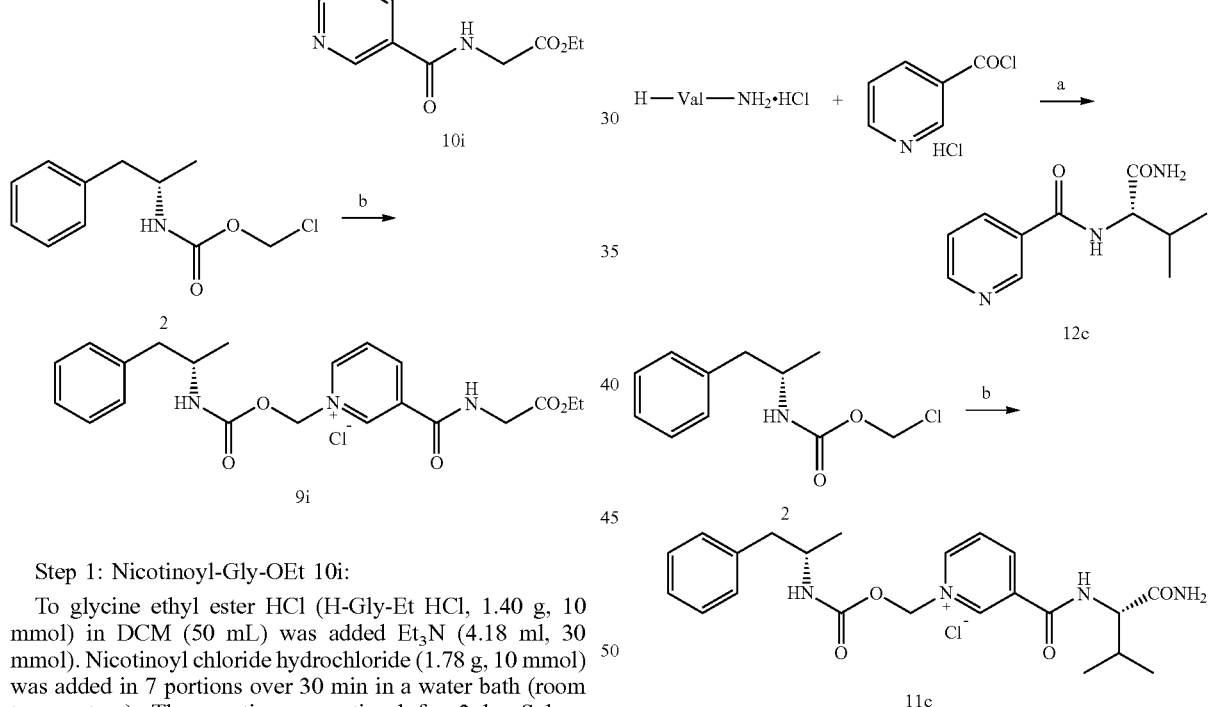

Step 1: Nicotinoyl-Gly-OEt 10i:

To glycine ethyl ester HCl (H-Gly-Et HCl, 1.40 g, 10 mmol) in DCM (50 mL) was added Et$_3$N (4.18 ml, 30 mmol). Nicotinoyl chloride hydrochloride (1.78 g, 10 mmol) was added in 7 portions over 30 min in a water bath (room temperature). The reaction was stirred for 2 hr. Subsequently, 5% of aq. NaHCO$_3$ (40 mL) was added to quench the reaction, followed by 50 ml of DCM. The DCM layer was further washed with 5% of aq. NaHCO$_3$ (40 mL) and dried over Na$_2$SO$_4$. The product was purified by silica gel column chromatography (EtOAc). 1.59 g of 10a was obtained as syrup. The yield was 76%.

Step 2: AMP-CO$_2$—CH$_2$-nicotinoyl-Gly-OEt 9i:

Nicotinoyl-Gly-OEt 10i (0.167 g, 0.8 mmol), ClCH$_2$OCO-AMP 2 (0.209 g, 0.92 mmol) and NaI (0.127 g, 0.848 mmol) in acetonitrile (8 mL) were heated at 65° C. for 1 hr. The solid was filtered off. The filtrate was concentrated to dryness and then dissolved in 6 mL of ethanol and treated with Dowex 1×8 twice (200-400, Cl form, 1 g and 0.5 g). The filtrate, after resin treatment, was concentrated to dry- Step 1: Nicotinoyl-Val-NH$_2$ 12c:

To valine amide HCl (H-Val-NH$_2$ HCl, 0.458 g, 3 mmol) in DCM (30 mL) was added Et$_3$N (1.062 g, 10.5 mmol). Nicotinoyl chloride hydrochloride (0.587 g, 3.3 mmol) was added in 3 portions over 10 min under a water bath (room temperature). The reaction was stirred for 1.5 hr. Solvent was evaporated. The remaining solid was purified by silica column gel chromatography (8% MeOH/DCM) to give a white solid which contained Et$_3$N HCl. To the solid was added ethanol (10 mL) and the mixture was heated to reflux (solid did not dissolve completely). The mixture was cooled to room temperature. Solid was collected after 2 hr, washed with ethanol (1 mL×3), and dried over vacuum. 0.245 g of 12c was obtained. The yield was 36.9%.

Step 2: AMP-CO₂CH₂-nicotinoyl-Val-NH₂ 11c:

Nicotinoyl-Val-NH₂ 12c (0.111 g, 0.5 mmol), ClCH₂OCO-AMP 2 (0.137 g, 0.6 mmol) and NaI (0.086 g, 0.575 mmol) in acetone (6 mL) were refluxed for 1.5 hr. The solid was filtered off. The filtrate was concentrated to dryness, the resulting residue dissolved in 6 mL of ethanol and treated with Dowex 1×8 twice (200-400, Cl form, 0.8 g and 0.4 g). The filtrate, after resin treatment, was concentrated and dried over vacuum to give 0.218 g of 11c as an amorphous solid. The yield was 97%.

Synthesis of Amphetamine Double Conjugate (AMP-CO₂CH₂-nicotinoyl)₂-Ser-OMe 13b:

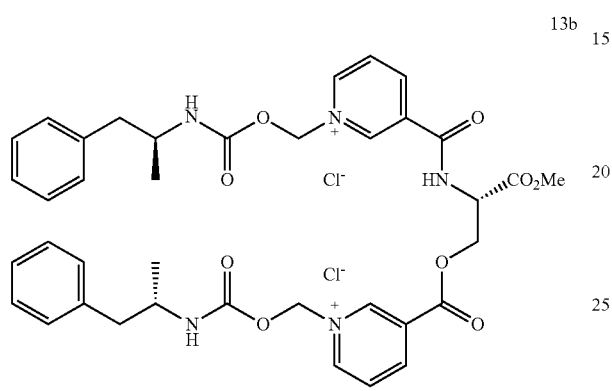

13b

Synthetic Scheme for (AMP-CO₂CH₂-nicotinoyl)₂-Ser-OMe 13b:

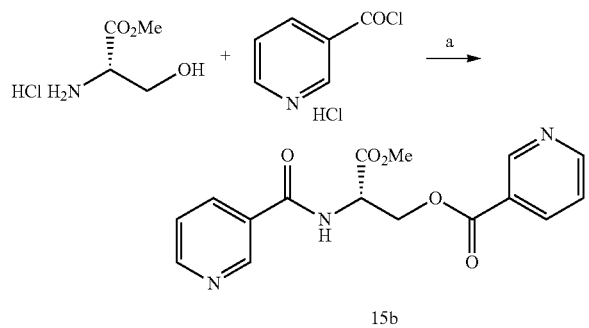

15b

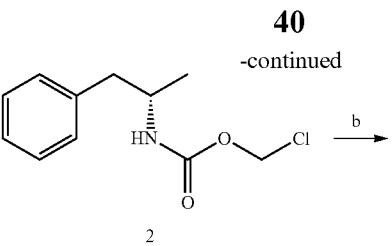

2

13b

Step 1: (Nicotinoyl)₂-Ser-OMe 15b:

To serine methyl ester HCl (2.80 g, 18 mmol) in DCM (200 mL) was added Et₃N (14.57 g, 144 mmol). Nicotinoyl chloride hydrochloride (9.613 g, 54 mmol) was added in 7 portions over 30 min in a water bath (room temperature). The reaction was stirred for 22 hr. Subsequently, 5% of aq. NH₄Cl (80 mL) was added to quench the reaction. The DCM layer was dried over Na₂SO₄. The product was purified by silica gel column chromatography (EtOAc, then 7% MeOH/DCM). 3.99 g of 15b was obtained as syrup. The yield was 67%.

Step 2: (AMP-CO₂CH₂-nicotinoyl)₂-Ser-OMe 13b:

(Nicotinoyl)₂-Ser-OMe 15b (0.165 g, 0.5 mmol), ClCH₂OCO-AMP 2 (0.273 g, 1.2 mmol) and NaI (0.172 g, 1.15 mmol) in acetone (12 mL) were refluxed for 1.5 hr. The solid was filtered off. The filtrate was concentrated to dryness, the resulting residue dissolved in 8 mL of methanol and treated with Dowex 1×8 twice (200-400, Cl form, 1.5 g, 1 g). The filtrate, after resin treatment, was concentrated and dried over vacuum to give 0.334 g of 13b as an amorphous solid. The yield was 85%.

Conjugates could be different salt forms other than chloride salt.

| Structure | Structure |
|---|---|
| 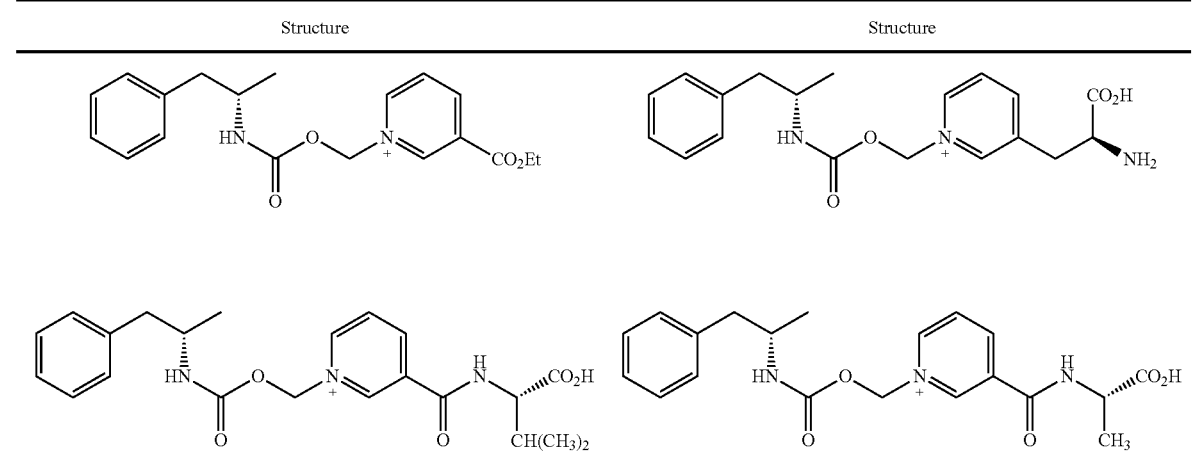 | |

| Structure | Structure |
|---|---|

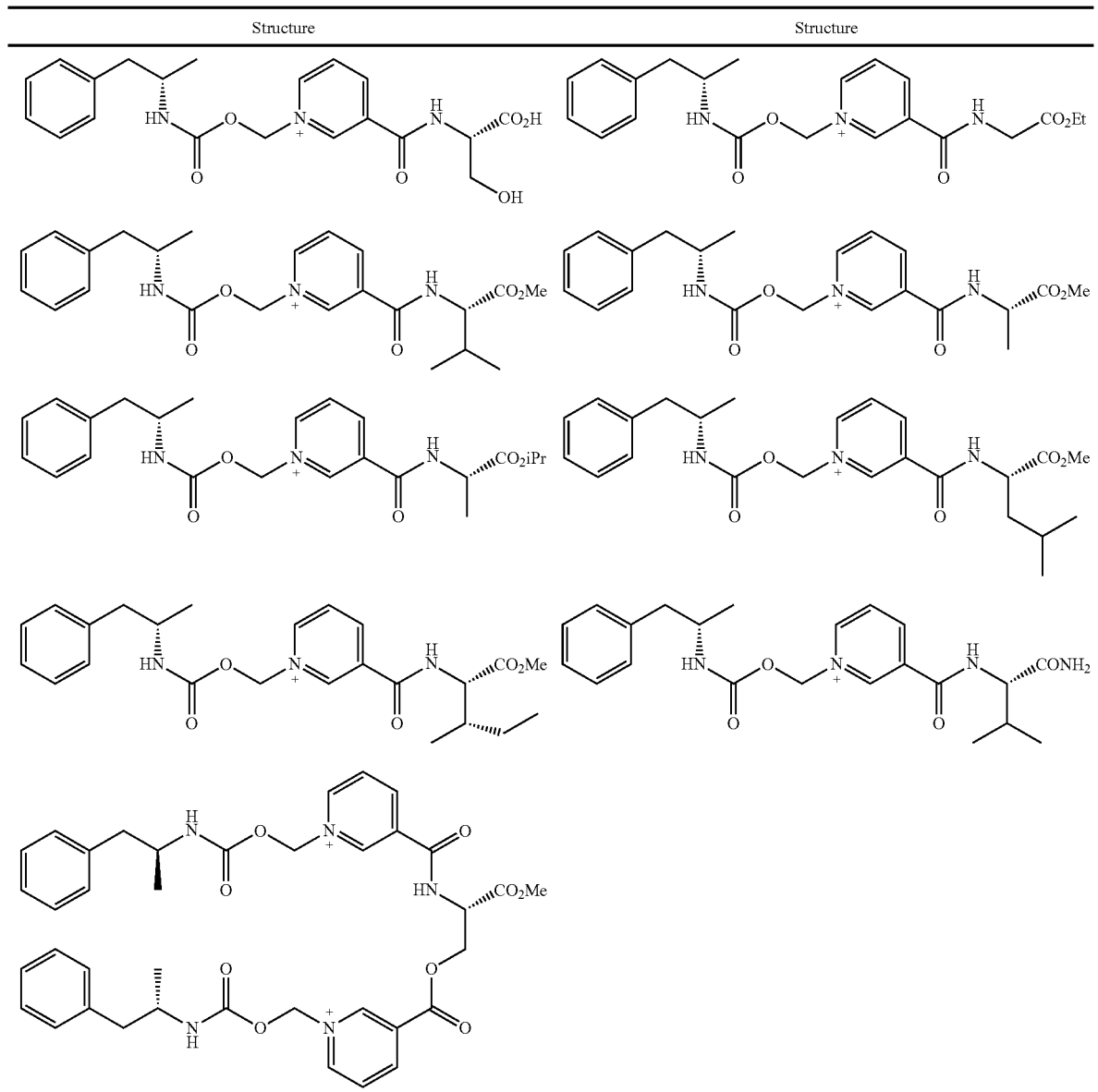

For the following aspects of the invention, $^1$H-NMR and $^{13}$C-NMR were recorded on a Bruker Advance II 500 spectrometer with DMSO-$d_6$ as solvent (no internal standard). Low resolution ESI mass spectra were recorded on an Agilent 1290 HPLC and Agilent 6420 QQQ Triple Mass Spectrometer, run in a positive ion mode, using 0.1% formic acid-water/0.1% formic acid-acetonitrile as mobile base. HPLC was run on an Agilent 1200 Series instrument with a YMC ODS-AQ (C-18, 4.6×250 mm, 5 μm, 120 Å) column and 0.1% TFA-water/0.1% TFA-acetonitrile as mobile phase.

| Structure | MW | Purity (%) | NMR | m.p. (° C.) |
|---|---|---|---|---|
| 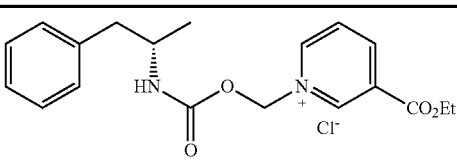<br>AMP-CO$_2$CH$_2$-nicotinate(Et) | 378.85 | 96 | $^1$H, $^{13}$C | NA |

-continued

| Structure | MW | Purity (%) | NMR | m.p. (° C.) |
|---|---|---|---|---|
| AMP-CO$_2$CH$_2$-nicotinoyl-Val-NH$_2$ | 448.95 | 98 | $^1$H, $^{13}$C | NA |

NA: compounds were amorphous and melting point could not be determined

Example 1: Oral Pharmacokinetic Study

Conjugates of d-amphetamine, and d-amphetamine sulfate or lisdexamfetamine dimesylate comparator compound were dissolved in an appropriate vehicle and administered in rats via oral gavage at doses of 5.6 μmol/kg. Whole blood samples were collected via retro-orbital bleeding at 0.25, 0.5, 1, 2, 4, and optionally at 3 and 6 hours postdose. Blood samples were centrifuged and the resulting plasma samples were collected for analysis of amphetamine concentrations by LC-MS/MS.

The oral pharmacokinetic plasma concentration-time profiles are shown in FIGS. 1-10. A summary of the oral pharmacokinetic parameters is provided in Table 6 and Table 7.

TABLE 6

Oral PK Parameters for d-Amphetamine Conjugates Administered in Rat Using a 4-hour Time Course

| Conjugate | $C_{max}$ (ng/mL) | AUC$_{0-4\ hr}$ (hr*ng/mL) | $T_{max}$ (hours) |
|---|---|---|---|
| AMP-CO$_2$CH$_2$-nicotinate(Et) | 47.9 | 119.2 | 1.7 |
| AMP-CO$_2$CH$_2$-nicotinoyl-Ser | 29.7 | 83.7 | 1.7 |

TABLE 7

Oral PK Parameters for d-Amphetamine Conjugates Administered in Rat Using a 6-hour Time Course

| Conjugate | $C_{max}$ (ng/mL) | AUC$_{0-4\ hr}$ (hr*ng/mL) | AUC$_{0-6\ hr}$ (hr*ng/mL) | $T_{max}$ (hours) |
|---|---|---|---|---|
| AMP-CO$_2$CH$_2$-nicotinoyl-Ala-OMe | 66.1 | 167.5 | 233.5 | 1.7 |
| AMP-CO$_2$CH$_2$-nicotinoyl-Val-NH$_2$ | 52.1 | 125.8 | 176.7 | 1.7 |
| (AMP-CO$_2$CH$_2$-nicotinoyl)$_2$-Ser-OMe | 40.5 | 104.0 | 152.8 | 2.8 |

Example 2: Intravenous Pharmacokinetic Study

Conjugates of d-amphetamine, and d-amphetamine sulfate or lisdexamfetamine dimesylate comparator compound were dissolved in an appropriate vehicle and administered in rats at doses of 5.6 μmol/kg by injecting the solution into the tail vein. Whole blood samples were collected via retro-orbital bleeding at 5 minutes and at 0.25, 0.5, 1 and 2 hours postdose. Blood samples were centrifuged and the resulting plasma samples were collected for analysis of levorphanol concentrations by LC-MS/MS.

A summary of the intravenous pharmacokinetic parameters of d-amphetamine is provided in Table 8.

TABLE 8

Intravenous PK Parameters for d-Amphetamine Conjugates Administered in Rat

| Conjugate | $C_{max}$ (ng/mL) | AUC$_{0-2\ hr}$ (hr*ng/mL) | $T_{max}$ (hours) |
|---|---|---|---|
| AMP-CO$_2$CH$_2$-nicotinate(Et) | 14.6 | 23.9 | 1.25 |
| AMP-CO$_2$CH$_2$-nicotinoyl-Ala-OMe | 57.6 | 79.5 | 0.90 |
| AMP-CO$_2$CH$_2$-nicotinoyl-Val-NH$_2$ | 73.8 | 108.3 | 0.80 |

Example 3: Intranasal Pharmacokinetic Study

Conjugates of d-amphetamine, and d-amphetamine sulfate or lisdexamfetamine dimesylate comparator compound were dissolved in an appropriate vehicle and administered in rats at doses of 5.6 μmol/kg by slowly adding the respective dosing solution drop-wise and alternating into the nasal openings. Whole blood samples were collected via retro-orbital bleeding at 5 minutes and at 0.25, 0.5, and 1 hours postdose. Blood samples were centrifuged and the resulting plasma samples were collected for analysis of amphetamine concentrations by LC-MS/MS.

A summary of the intranasal pharmacokinetic parameters is provided in Table 9.

TABLE 9

Intranasal PK Parameters for d-Amphetamine Conjugates Administered in Rat

| Conjugate | $C_{max}$ (ng/mL) | AUC$_{0-1\ hr}$ (hr*ng/mL) | $T_{max}$ (hours) |
|---|---|---|---|
| AMP-CO$_2$CH$_2$-nicotinate(Et) | 113.6 | 76.1 | 0.12 |
| AMP-CO$_2$CH$_2$-nicotinoyl-Val-NH$_2$ | 102.2 | 39.6 | 0.08 |

Figure 8:
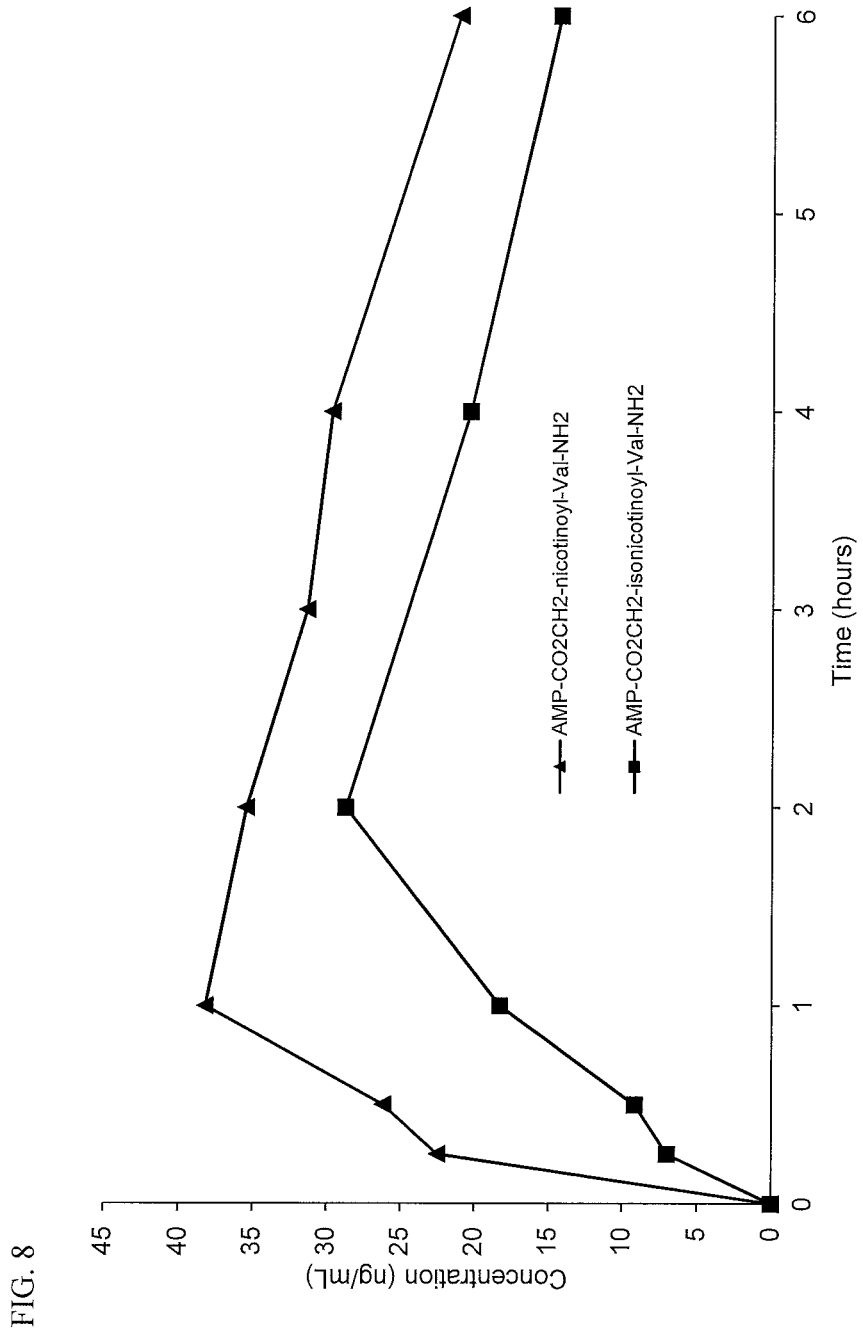
FIG. 8. Oral PK curves comparing d-amphetamine-$CO_2CH_2$-nicotinoyl-valinamide (AMP-$CO_2CH_2$-nicotinoyl-Val-$NH_2$) and d-amphetamine-$CO_2CH_2$-isonicotinoyl-valinamide (AMP-$CO_2CH_2$-isonicotinoyl-Val-$NH_2$).
Figure 9:
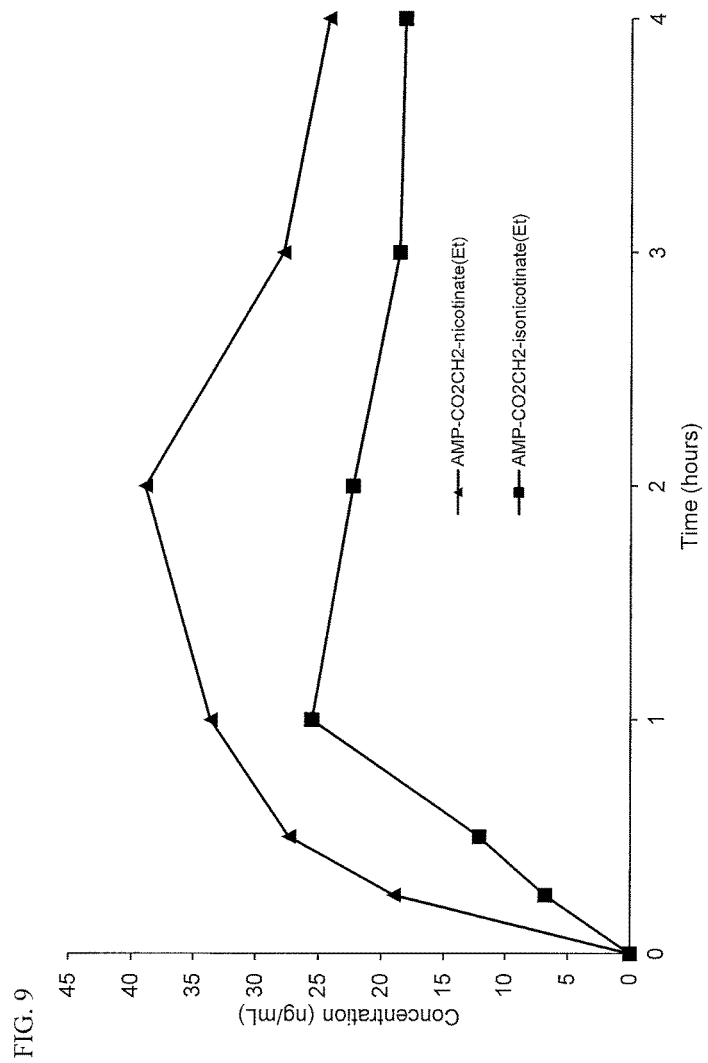
FIG. 9. Oral PK curves comparing d-amphetamine-$CO_2CH_2$-nicotinate ethyl ester (AMP-$CO_2CH_2$-nicotinate (Et)) and d-amphetamine-$CO_2CH_2$-isonicotinate ethyl ester (AMP-$CO_2CH_2$-isonicotinate(Et)).
Figure 10:
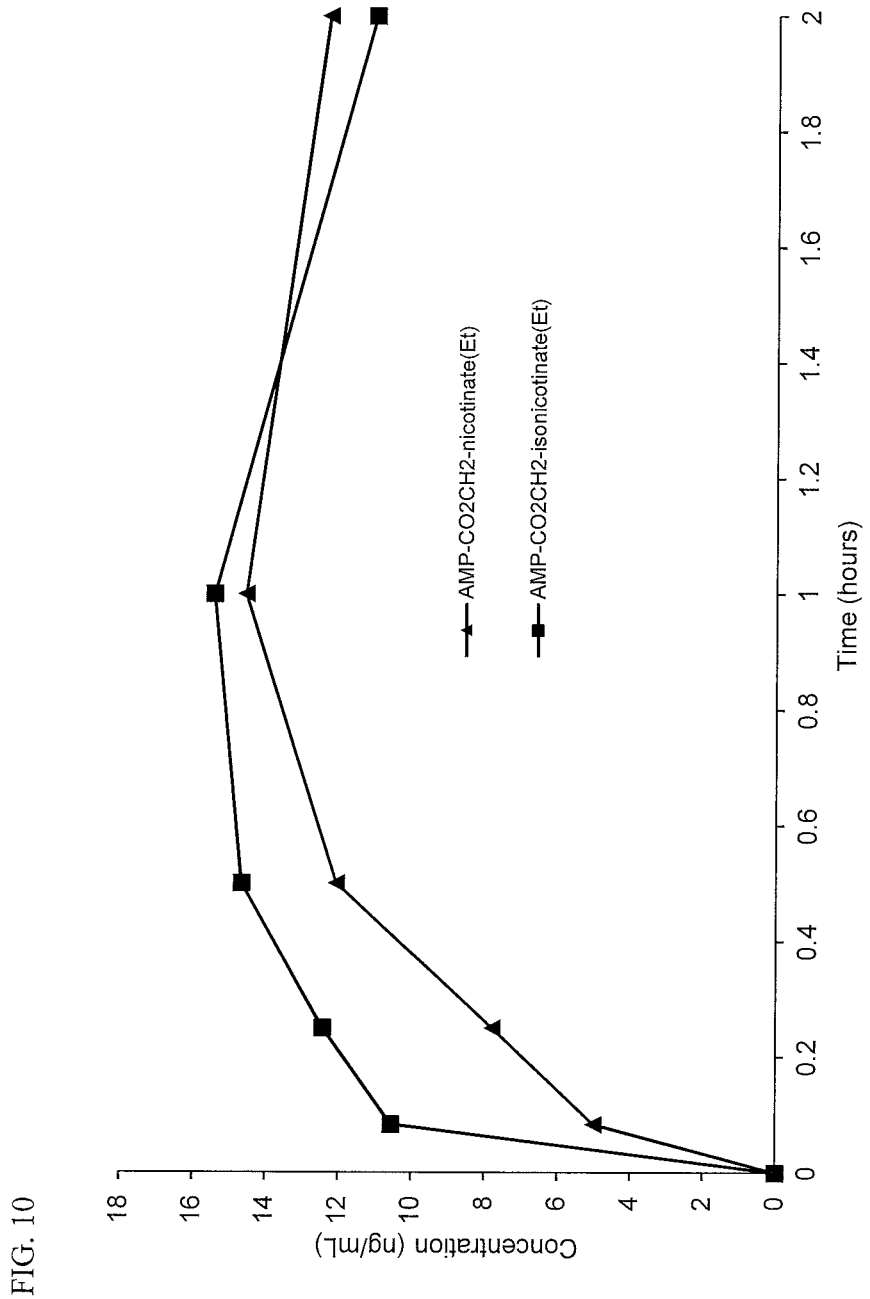
FIG. 10. Intravenous PK curves comparing d-amphetamine-$CO_2CH_2$-nicotinate ethyl ester (AMP-$CO_2CH_2$-nicotinate(Et)) and d-amphetamine-$CO_2CH_2$-isonicotinate ethyl ester (AMP-$CO_2CH_2$-isonicotinate(Et)).

FIG. 8-10 illustrate that some compounds of the present invention containing an nicotinoyl moiety unexpectedly and non-obviously result in different and/or improved d-amphetamine exposure following oral, intranasal, and/or intravenous administration in a subject when compared to a compound of the same structure but with the nicotinoyl replaced by a isonicotinoyl moiety. FIG. 8 illustrates d-amphetamine-CO$_2$CH$_2$-nicotinoyl-Val-NH$_2$ provides increased oral bioavailability of d-amphetamine compared to d-amphetamine-CO$_2$CH$_2$-isonicotinoyl-Val-NH$_2$. FIG. 9 illustrates, d-amphetamine-CO₂CH₂-nicotinate(Et) provides increased oral bioavailability of d-amphetamine compared to d-amphetamine-CO₂CH₂-isonicotinate(Et). FIG. 10 illustrates, AMP-CO₂CH₂-nicotinate(Et) decreases exposure to d-amphetamine after intravenous administration when compared to AMP-CO₂CH₂-isonicotinate(Et).

Further aspects and embodiments of the present technology are described in the following paragraphs.

One aspect of the present invention is a compound having the structure of Formula I:

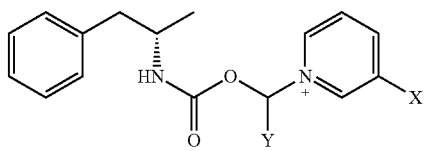

or a pharmaceutically acceptable salt thereof, where X is selected from the group consisting of esters, carboxylic acids, amino acids, amino acid residues, amides, and derivatives thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle. Another aspect is a composition comprising the compound or pharmaceutically acceptable salt of the compound.

Another aspect of the present invention is a compound having the structure of Formula IB or the pharmaceutically acceptable salt of said compound:

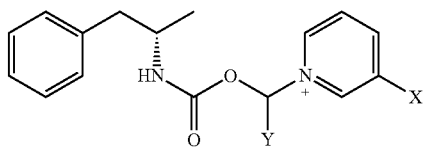

where X is A-COO—R;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. Another aspect is a composition comprising the compound or pharmaceutically acceptable salt of the compound.

Another aspect of the present invention is a compound having the structure of Formula ID or the pharmaceutically acceptable salt of said compound:

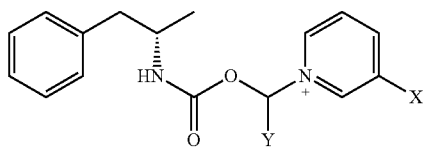

where X is A-CO—NR¹R²;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R¹ and R² are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. Another aspect is a composition comprising the compound or pharmaceutically acceptable salt of the compound.

Another aspect of the present invention is a compound or the pharmaceutically acceptable salt of said compound, wherein A is absent, Y is hydrogen, and the compound has the structure of formula IIB:

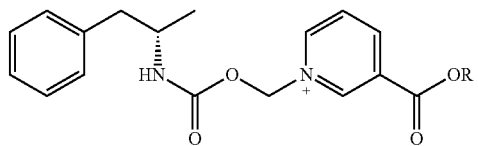

where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. Another aspect is a composition comprising the compound or pharmaceutically acceptable salt of the compound.

Another aspect is a compound or a pharmaceutically acceptable salt of said compound, wherein A is absent, Y is hydrogen, and the compound has the structure of Formula IID:

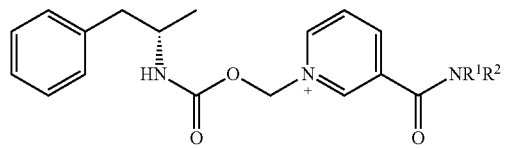

where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. Another aspect is a composition comprising the compound or pharmaceutically acceptable salt of the compound.

In yet another aspect, a compound has a structure selected from the group consisting of:

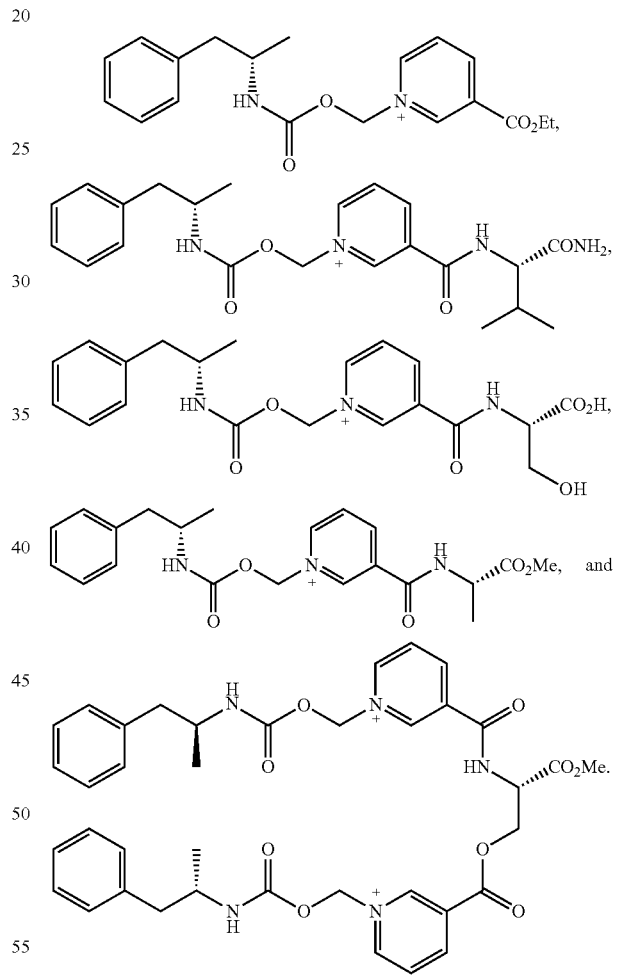

In one aspect, the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In another aspect, the compound has a structure selected from the group consisting of:

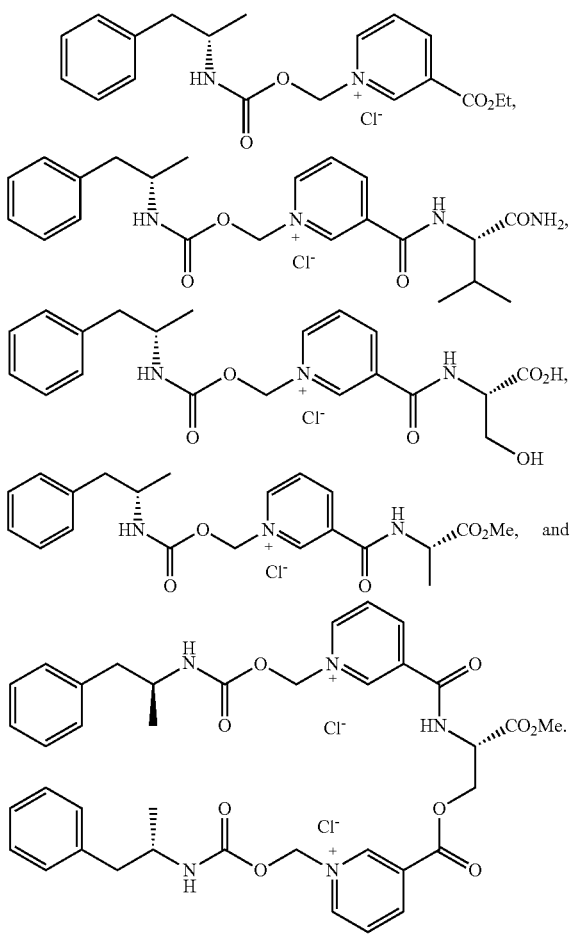

One aspect of the present invention is a composition comprising any compound of the present invention or pharmaceutically acceptable salt of the compound. In one aspect, the composition is formulated for oral administration or suppository administration. In a further aspect, the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension. In another aspect, the composition further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof. In a further aspect, the binder is selected from the group consisting of hydroxypropylmethyl cellulose, ethyl cellulose, povidone, acrylic and methacrylic acid co-polymers, pharmaceutical glaze, gums, and milk derivatives.

In one aspect, the compound is present in an amount per unit dose of between about 0.1 mg and about 2000 mg per unit dose. In another aspect, the compound is present in an amount per unit dose of between about 0.5 mg and about 500 mg per unit dose. In a further aspect, the compound is present in an amount per unit dose of between about 1 mg and about 250 mg per unit dose. In yet another aspect, the compound is present in an amount per unit dose of between about 1.5 mg and about 100 mg per unit dose.

In one aspect, the composition further comprises one or more additional pharmacological substance selected from the group consisting of stimulants, anti-depressants, combinations thereof and prodrugs thereof. In another aspect, the composition further comprises one or more of methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, or one or more of additional amphetamine, or any combination of the foregoing. In a further aspect, the one or more additional amphetamine is unconjugated amphetamine, a conjugate of amphetamine, a prodrug of amphetamine, any isomer thereof, or any combination thereof. In yet another aspect, the isomer of unconjugated amphetamine is unconjugated d-amphetamine. In a further aspect, the methylphenidate is unconjugated methylphenidate, a conjugate of methylphenidate, a prodrug of methylphenidate, any isomer thereof, or any combination thereof. In another aspect, the isomer of unconjugated methylphenidate is unconjugated d-methylphenidate. In yet another aspect, the conjugate of methylphenidate is serdexmethylphenidate.

In one aspect, the compound is provided in an amount sufficient to provide a similar or decreased AUC when compared to unconjugated d-amphetamine when orally administered at equimolar doses. In another aspect, the compound is provided in an amount sufficient to provide a similar or decreased $C_{max}$ as compared to unconjugated d-amphetamine when administered orally at equimolar doses. In yet another aspect, the compound is provided in an amount sufficient to provide a decreased $C_{max}$ and a similar or decreased AUC as compared to unconjugated d-amphetamine when administered orally at equimolar doses. In one aspect, intranasal or intravenous administration of the compound provides a decreased AUC and/or $C_{max}$ when compared to an equivalent molar amount of unconjugated d-amphetamine. In another aspect, the compound provides reduced abuse potential as compared to unconjugated d-amphetamine.

One aspect of the present invention is a kit comprising individual doses of a therapeutically effective amount of a composition comprising the compound of claim 1, a pharmaceutical salt thereof, or a combination thereof.

One aspect of the present invention is a method of treating a patient having a disorder or condition requiring stimulation of the central nervous system, of treating a patient having a disease, disorder or condition mediated by controlling, preventing, limiting, or inhibiting neurotransmitter uptake, or treating a patient having a disease, disorder or condition mediated by increasing neurotransmitter concentrations in the synapse, the method comprising the step of administering to the patient in need thereof a pharmaceutically effective amount of the composition of claim 9. In another aspect, the composition has reduced abuse potential when administered compared to unconjugated d-amphetamine. In yet another aspect, the disease or condition is attention-deficit hyperactivity disorder, attention deficit disorder, autistic spectrum disorder, autism, Asperger's disorder, pervasive developmental disorder, sleep disorder, obesity, depression, bipolar disorder, eating disorder, chronic fatigue syndrome, insomnia, schizophrenia, major depressive disorder, narcolepsy, postural orthostatic tachycardia syndrome, Tourette syndrome, nervous tics, substance use disorder, lethargy, depression, neural insult or obesity.

The presently described technology is now described in such full, clear, concise and exact terms as to enable any person skilled in the art to which it pertains, to practice the same. It is to be understood that the foregoing describes preferred aspects of the invention and that modifications may be made therein without departing from the spirit or scope of the invention.

What is claimed is:

1. A compound having a structure selected from the group consisting of:

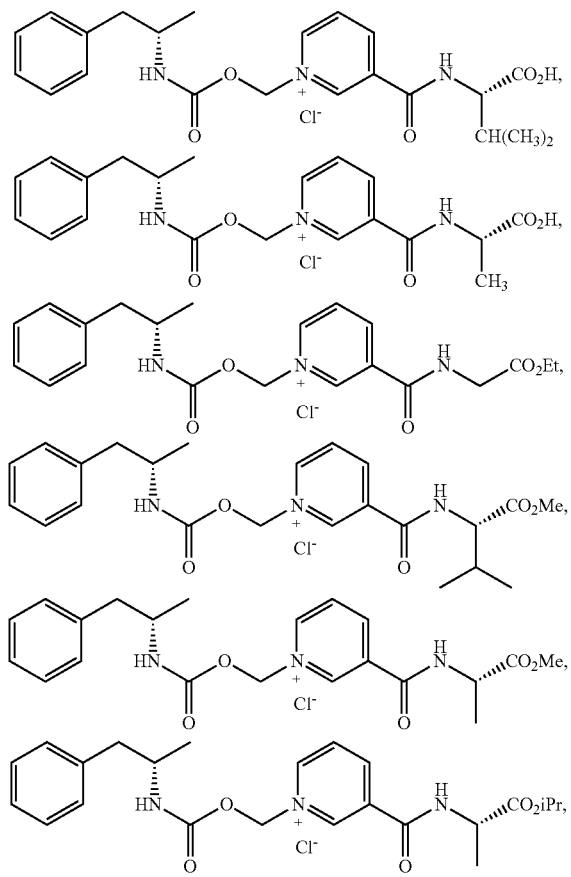

2. A compound having a structure selected from the group consisting of:

or a pharmaceutically acceptable salt thereof.

3. The compound of claim 2, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicyl sulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

4. A composition comprising the compound of claim 1.

5. A composition comprising the compound of claim 2 or pharmaceutically acceptable salt of the compound.

6. The composition of claim 4, wherein the composition is formulated for oral administration or suppository administration.

7. The composition of claim 5, wherein the composition is formulated for oral administration or suppository administration.

8. The composition of claim 6, wherein the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension.

9. The composition of claim 7, wherein the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension.

10. The composition of claim 8, wherein the composition further comprises one or more excipients, wherein the excipients are selected from the group consisting of antiadherents, binders, coatings, disintegrants, fillers, flavors, dyes, colors, glidants, lubricants, preservatives, sorbents, sweeteners, derivatives thereof, and combinations thereof.

11. The composition of claim 9, wherein the composition further comprises one or more excipients, wherein the excipients are selected from the group consisting of antiadherents, binders, coatings, disintegrants, fillers, flavors, dyes, colors, glidants, lubricants, preservatives, sorbents, sweeteners, derivatives thereof, and combinations thereof.

12. The composition of claim 10, wherein the binder is selected from the group consisting of hydroxypropylmethyl cellulose, ethyl cellulose, povidone, acrylic and methacrylic acid co-polymers, pharmaceutical glaze, gums, and milk derivatives.

13. The composition of claim 11, wherein the binder is selected from the group consisting of hydroxypropylmethyl cellulose, ethyl cellulose, povidone, acrylic and methacrylic acid co-polymers, pharmaceutical glaze, gums, and milk derivatives.

14. The composition of claim 4, wherein the compound is present in an amount per unit dose of between about 0.1 mg and about 2000 mg per unit dose.

15. The composition of claim 5, wherein the compound is present in an amount per unit dose of between about 0.1 mg and about 2000 mg per unit dose.

16. The composition of claim 4, wherein the composition further comprises one or more of methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, or one or more of additional amphetamine, or any combination thereof and/or one or more additional pharmacological substance selected from the group consisting of stimulants, anti-depressants, combinations thereof and prodrugs thereof.

17. The composition of claim 5, wherein the composition further comprises one or more of methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, or one or more of additional amphetamine, or any combination thereof and/or one or more additional pharmacological substance selected from the group consisting of stimulants, anti-depressants, combinations thereof and prodrugs thereof.

18. A kit comprising individual doses of a therapeutically effective amount of a composition comprising the compound of claim 1.

19. A kit comprising individual doses of a therapeutically effective amount of a composition comprising the compound of claim 2.

* * * * *

UNITED STATES PATENT AND TRADEMARK OFFICE
CERTIFICATE OF CORRECTION

| | | |
|---|---|---|
| PATENT NO. | : 12,091,386 B2 | Page 1 of 1 |
| APPLICATION NO. | : 17/500680 | |
| DATED | : September 17, 2024 | |
| INVENTOR(S) | : Guenther et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
Ninth Day of September, 2025

Coke Morgan Stewart
*Acting Director of the United States Patent and Trademark Office*